(12) United States Patent
Ishida et al.

(10) Patent No.: US 7,922,848 B2
(45) Date of Patent: Apr. 12, 2011

(54) TUBE CLAMP DEVICE AND TUBE CONNECTION DEVICE

(75) Inventors: Shinji Ishida, Isehara (JP); Satoshi Yamanushi, Nirasaki (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 573 days.

(21) Appl. No.: 10/562,829

(22) PCT Filed: Jun. 2, 2004

(86) PCT No.: PCT/JP2004/007617
§ 371 (c)(1),
(2), (4) Date: Dec. 29, 2005

(87) PCT Pub. No.: WO2005/000564
PCT Pub. Date: Jan. 6, 2005

(65) Prior Publication Data
US 2006/0145105 A1    Jul. 6, 2006

(30) Foreign Application Priority Data

Jun. 30, 2003    (JP) .................................. 2003-187723

(51) Int. Cl.
*B31F 5/00*    (2006.01)
(52) U.S. Cl. ...................................................... 156/159
(58) Field of Classification Search ................ 156/158, 156/159, 304.2, 499; 604/250, 244, 533, 604/905; 292/247, 71, 109, 101, 202, DIG. 64
See application file for complete search history.

(56) References Cited

U.S. PATENT DOCUMENTS

| | | | | |
|---|---|---|---|---|
| 1,477,265 A | * | 12/1923 | Holstein | 292/202 |
| 4,516,971 A | * | 5/1985 | Spencer | 156/159 |
| 4,610,670 A | | 9/1986 | Spencer | |
| 4,619,642 A | * | 10/1986 | Spencer | 604/29 |

FOREIGN PATENT DOCUMENTS

EP    0 778 123 A2    6/1997
(Continued)

OTHER PUBLICATIONS

Babyak, Fascinating Fixtures, Jun. 1993, Appliance Manufacturer. Troy: vol. 41, iss. 6; p. 34.*

(Continued)

*Primary Examiner* — Kevin C Sirmons
*Assistant Examiner* — Bradley J Osinski
(74) *Attorney, Agent, or Firm* — Buchanan Ingersoll & Rooney PC

(57) ABSTRACT

A tube clamp apparatus and a tube connecting apparatus having high durability and improved operability when an operator locks these apparatuses are provided. A tube connecting apparatus comprises a first clamp and a second clamp, each pressing to hold two flexible tubes 8, 9. The tubes are placed at a lower jaw portion of the second clamp and pressed to a flat state by pressing force applied thereto a direction of an arrow F. A hook section 310 having hook portions divided into plural pieces is set up at an upper jaw portion of the second clamp, and the hook portion B 312 is made of a POM elastic member having, on one side thereof, a protruded portion 314 protruded from other adjacent hook portions. When pressing force is applied to the upper jaw portion, the hook portion B 312 protruded from the other adjacent hook portions is elastically deformed and engaged with a POM-made roller B 317 to prevent back-tracking of the hook section 310.

8 Claims, 17 Drawing Sheets

FOREIGN PATENT DOCUMENTS

| | | |
|---|---|---|
| JP | 60-34455 A | 2/1985 |
| JP | 61-30582 B2 | 7/1986 |
| JP | 2-27936 B2 | 6/1990 |
| JP | 04 161579 A | 6/1992 |
| JP | 4-308731 A | 10/1992 |
| JP | 6-091010 A | 4/1994 |
| JP | 9-154920 A | 6/1997 |

OTHER PUBLICATIONS

Smith and Fletcher, Gearing Up with Plastic, Sep. 1998, Mechanical Engineering; feature article.*

International Search Report dated Aug. 24, 2004.

European Search Report issued in Application No. EP 04 74 5516 dated Mar. 29, 2008.

English language translation of Office Action issued Jul. 31, 2007 in corresponding Japanese Application No. 2003-187723.

Office Action issued Aug. 17, 2007 in corresponding Canadian Application No. 2,531,158.

European Office Action dated Jan. 27, 2010 issued in the corresponding European Patent Application No. 04745516.7-1253.

* cited by examiner

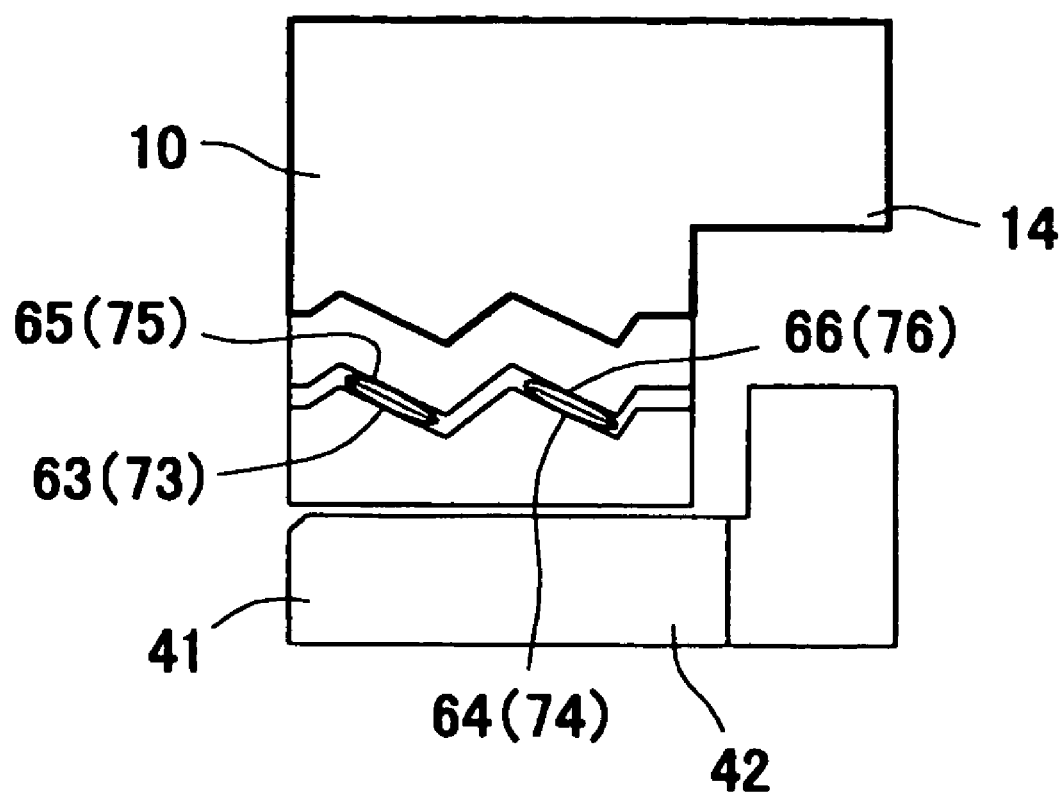

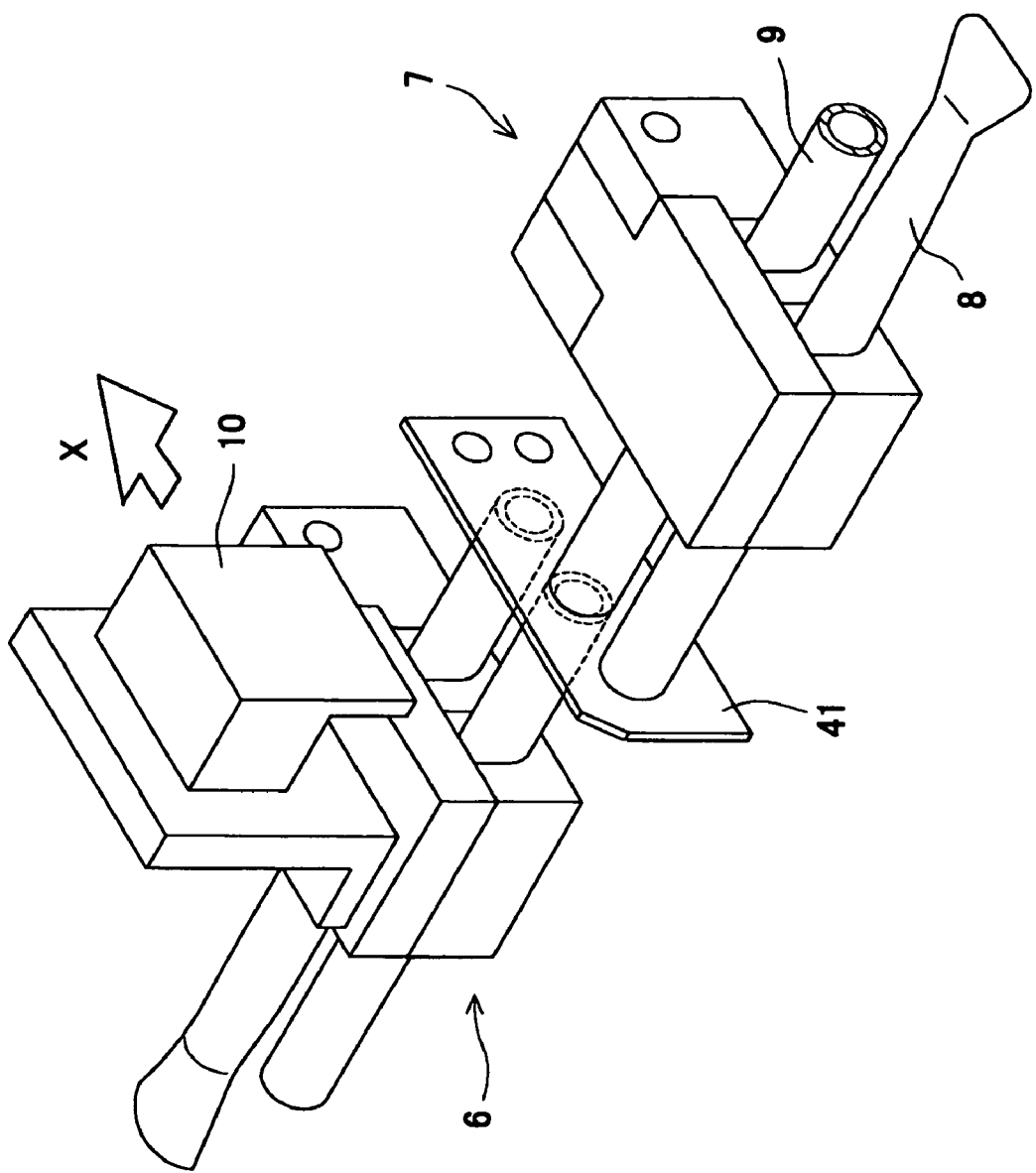

TUBE CLAMP DEVICE AND TUBE CONNECTION DEVICE

This application is a 371 of PCT/JP04/07617 filed Jun. 2, 2004 and claims foreign priority to Japanese Application No. 2003-187723 filed Jun. 30, 2003.

FIELD OF THE INVENTION

The present invention relates to a tube clamp apparatus and a tube connecting apparatus, and in particular relates to a tube clamp apparatus which presses to hold a flexible tube in a flat state and a tube connecting apparatus which connects flexible tubes each other.

DESCRIPTION OF RELATED ART

Conventionally, in a case that tube connecting between a blood-collecting bag and a blood-component bag in a blood transfusion system, exchanging between a dialytic-fluid bag and a waste-fluid bag in continuous ambulatory peritoneal dialysis (CAPD) or the like is carried out, it is necessary to connect tubes under a sterilized condition. For example, in JPB 61-30582, a tube connecting apparatus equipped with a pair of holders capable of holding two tubes to be connected in parallel and a cutting plate (plate-shaped heater element, wafer) capable of moving across the tubes which are placed between both of the holders is disclosed. In this tube connecting apparatus, the cutting plate is heated and moved to melt and cut the tubes in a state that the two tubes are held in parallel and in an opposite direction in grooves which are formed at the holders, then, one of the holders is moved in a diameter direction (row direction) of the tubes to coincide cut ends of the tubes to be connected each other, and the cutting plate is extracted by moving it to an evacuated position to fuse both of the tubes.

Further, for example, in JPA 6-91010, a tube connecting apparatus which employs the same tube connecting method as the above apparatus, which has a first clamp and a second clamp which hold two tubes in a parallel state, and which moves the first clamp in parallel to the second clamp, in order to improve reliability of tube connecting, is disclosed. The tube connecting apparatus has a first clamp movement mechanism that carries out merely forward or backward movement for advancing or retracting the first clamp, and a second clamp movement mechanism that moves the second clamp merely in a direction that the second clamp approaches/separates to/from the first clamp.

Furthermore, for example, in JPA 4-308731, a tube connecting apparatus, which employs the same principle of heating, melting and then connecting the tubes each other under a sterilized condition by utilizing a cutting plate, yet which connects the tubes in a state that liquid in the tubes is kept contained without leaking the liquid even in a case that the liquid remains inside the tubes before the tubes are cut, is disclosed. In this tube connecting apparatus, two tubes (a first tube, a second tube) are held on the same rotation locus respectively according to a pair of tube holders allowed to rotate relatively, after the two tubes are cut between the holders by a heated cutting plate, the tube holders are rotated such that a cut end face of one end side of the first tube aligns (corresponds to) a cut end face of another side of the second tube, and the cutting plate is evacuated to fuse both of the tubes. Moreover, for example, in JPA 9-154920, a tube connecting apparatus which is capable of not only connecting tubes in a state that liquid inside the tubes is kept contained and sealed without leaking the liquid but which can realize downsizing of the apparatus and of parts for the apparatus due to a small moving amount of the tubes at the time of connecting the tubes, is disclosed. In this tube connecting apparatus, two tubes to be connected are accommodated and held in two tube-holding assembly (a first tube-holding assembly, a second tube-holding assembly) in a contacted (piled) state with each other, after the two tubes are cut by a heated cutting plate, the second tube-holding assembly is rotated by 180 degrees relatively to the first tube-holding assembly such that cut end faces of the tubes are replaced with each other for alignment, and the cutting plate is evacuated to fuse both of the tubes.

In these conventional tube connecting apparatuses, because a cover, a covering body or the like of the clamp(s) for holding the tubes in a pressing state opens unexpectedly during connecting operation of the tubes, fixing of the tubes or pressing behavior of the clamp(s) to the tubes is canceled, which leads cutting or connecting operation to the tubes incomplete. For this reason, the tube connecting apparatus disclosed in the JPA 9-154920 has a pawl member formed to protrude at an internal surface of a plate piece which is provided pivotably with a hinge to the covering body at a tip of the covering body in the tube-holding assemblies, and a locking mechanism which locks (holds) the covering body so as not to open by rotating the plate piece in a state that the covering body is closed to engage the pawl member with a portion to be engaged formed at a tip of a holder at which the tubes are placed.

In such a locking mechanism, in general, such a device is made that a hook member such as a pawl member or the like and an engagement member for engaging the hook member are made of metal having high rigidity, that a protrusion is formed at a tip portion of the hook member, or that, by employing the both, holding power to the covering body is made larger so as the covering body not to open due to unexpected back-tracking of the hook member.

SUMMARY OF THE INVENTION

Problem to be Solved by the Invention

The conventional tube connecting apparatuses can maintain holding power by employing the above stated structures, but they request an operator large pressing force (load) at a time of locking the covering body so as the covering body not to open with a hook member, which lowered operability or work efficiency remarkably. Further, because the hook member and the engagement member are made of metal having high rigidity, abrasion is caused (parts are worn away) at a time of engagement operation therebetween. This weakens locking power (power for maintaining pressing state against the tube(s)) between the both, depending that the mechanism is going on use, consequently, there was a case that the mechanism had a difficulty in maintaining pressing force against the tube(s) in a proper flat state.

In view of the above circumstances, a problem to be solved by the present invention is to provide a tube clamp apparatus which has high durability and of which operability is improved when an operator locks the apparatus and a tube connecting apparatus equipped with the tube clamp apparatus.

Means for Solving the Problem

In order to solve the above problem, a first aspect of the present invention is directed to a tube clamp apparatus which presses to hold a flexible tube in a flat state, comprising: a placement clamp section at which the tube is placed; a movable clamp section which is movable in a direction of pressing the tube which is placed at the placement clamp section and in a direction of separating from the tube; and a hook section which is set up at the movable clamp section and which engages the placement clamp section to maintain a pressing state of the movable clamp section against the tube, wherein the hook section has a plurality of divided hook portions, and wherein at least one of the hook portions has a protruded portion which protrudes toward one side thereof than other hook portions and is made of an elastic member which maintains engagement with the placement clamp section.

In the first aspect, the flexible tube is placed at the placement clamp section, and the tube is pressed to a flat state according to pressing force to the movable clamp section applied in a direction of pressing the tube. The hook section having a plurality of divided hook portions is set up at the movable clamp section, and at least one of the hook portions is constituted by an elastic member having a protruded portion which protrudes toward one side thereof than other hook portions. When pressing force is applied to the movable clamp section, the elastic member which protrudes than the other hook portions deforms elastically to engage the placement clamp section together with the other hook portions, and the protruded portion of the elastic member maintains engagement with the movable clamp section to prevent the hook section from back-tracking, thereby a pressing state against the tube is maintained. On the other hand, when force in a direction opposite to the pressing force is applied in a direction of separating from the tube to the movable clamp section, the elastic member deforms elastically to cancel engagement with the placement clamp section, thereby the pressing state against the tube is canceled. According to the first aspect, because the elastic member deforms elastically and the protruded portion engages the movable clamp section, since pressing force applied to the movable clamp can be smaller than that of the conventional tube clamp apparatus while maintaining engagement between the placement clamp section and the movable clamp section, operability for an operator can be enhanced.

In the first aspect, when the elastic member is made of resin having a flexure property of bending so as to change its self-shape according to external pressure, because the protruded portion which engages the placement clamp section is made of resin and the elastic member bends, the elastic member is prevented from being worn away in comparison with a case in which metal members having high rigidity were used for the material conventionally and an operator can get off with small pressing force to the movable clamp section. Accordingly, not only durability of the placement clamp section and the hook section is enhanced but durability of the tube clamp apparatus is improved. Further, when the hook section is divided into plural pieces in a direction orthogonal to a longitudinal direction of the tube placed at the placement clamp section and another side of the elastic member is fixed to the hook section, the elastic member is provided with spring function to encourage the flexure property. Accordingly, operability and durability are more enhanced. At this time, the elastic member may be disposed at a center of the hook portions which are provided parallel and a material of the other hook portions may be made of metal. In such an embodiment, when the placement clamp section has an engagement member which engages the protruded portion of the elastic member and a material of the engagement member is made of resin, since both of the protruded portion to engage and the engagement member are made of resin to lower the parts being worn away, it is preferable in view of enhancing durability. Further, the engagement member may be a rotatable roller, and the protruded portion of the elastic member may slide to contact a circumferential surface of the roller to be located to an engagement maintaining position at which the protruded portion maintains engagement with the roller. In this case, it is preferable in operability and durability that the elastic member is set such that reaction force caused at a time of elastic deformation against external force is smaller than pressing force of the hook portions due to the hook section when the movable clamp section presses the tube to a flat state and is larger than or equal to load force against the protruded portion of the engagement member.

Further, in order to solve the above problem, a second aspect of the present invention is directed to a tube connecting apparatus which connects flexible tubes each other, comprising: a holding unit having a placement clamp section at which the tube is placed, a movable clamp section which is movable in a direction of pressing the tube which is placed at the placement clamp section and in a direction of separating from the tube, and a hook section which is set up at the movable clamp section and which engages the placement clamp section to maintain a pressing state of the movable clamp section against the tube; a cutting unit which cuts the tubes held in a flat state by the holding unit; and a movement unit which moves the holding unit to change relatively positions of the tubes cut by the cutting unit such that end portions to be connected face each other, wherein the holding unit has a plurality of divided hook portions at the hook section, and wherein at least one of the hook portions has a protruded portion which protrudes toward one side thereof than other hook portions and is made of an elastic member which maintains engagement with the placement clamp section.

In the second aspect, the holding unit corresponds to the tube clamp apparatus in the first aspect. Namely, the elastic member deforms elastically to engage the protruded portion with the placement clamp section, so that the tubes are held in a flat state by the holding unit. The tubes held by the holding unit are cut by the cutting unit, then, the holding unit is driven to move by the movement unit to change relatively positions of the tubes cut by the cutting unit such that end portions to be connected contact closely each other, thereby the tubes are connected. According to the second aspect, in the same manner as the first aspect, since pressing force applied to the movable clamp section can be small, operability for an operator can be enhanced. Further, because parts can be lowered in being worn away at a time of engagement operation, the holding unit holds the tubes in an appropriate flat state even in high frequency of use. Accordingly, cutting and connecting of the tubes according to the cutting unit and the movement unit are carried out properly.

In the second aspect, the holding unit may have a first holding section and a second holding section which are disposed along a longitudinal direction of the tubes placed at the placement clamp section and the cutting unit may cut the tubes between the first holding section and the second holding section. Further, the movement unit may move at least one of the first holding section and the second holding section in a direction of the longitudinal direction of the tubes placed at the placement clamp section and in a direction orthogonal to the tubes. At this time, it is preferable that the elastic member is made of resin having a flexure property of bending so as to change its self-shape according to external pressure, and it is more preferable that the elastic member is disposed at a center of the hook portions which are provided parallel and a material of the other hook portions is made of metal.

EFFECTS OF THE INVENTION

According to the first aspect of the present invention, because the elastic member of the movable clamp deforms elastically to engage the protruded portion with the movable clamp section, since pressing force applied to the movable clamp can be smaller than that of the conventional tube clamp apparatus while maintaining engagement between the placement clamp section and the movable clamp section, an effect that operability for an operator can be enhanced, can be obtained.

According to the second aspect, in addition to the effect in the first aspect, because parts can be lowered in being worn away at a time of engagement operation, since the holding unit holds the tubes in an appropriate flat state even in high frequency of use, an effect that cutting and connecting of the tubes according to the cutting unit and the movement unit are carried out properly, can be obtained.

BRIEF DESCRIPTION OF THE DRAWINGS

FIG. 11 is a side view showing a state of evacuating the wafer from a cutting position by descending a wafer holder which holds the wafer;

FIG. 17 is a perspective view showing operation of the main portions of the tube connecting apparatus in tube connecting process.

DETAILED DESCRIPTION OF THE PREFERRED EMBODIMENTS

With reference to the drawings, an embodiment of a tube connecting apparatus that cuts and then connects two tubes in which blood is contained and sealed and to which the present invention is applied will be explained.

(Structure)

Figure 1:
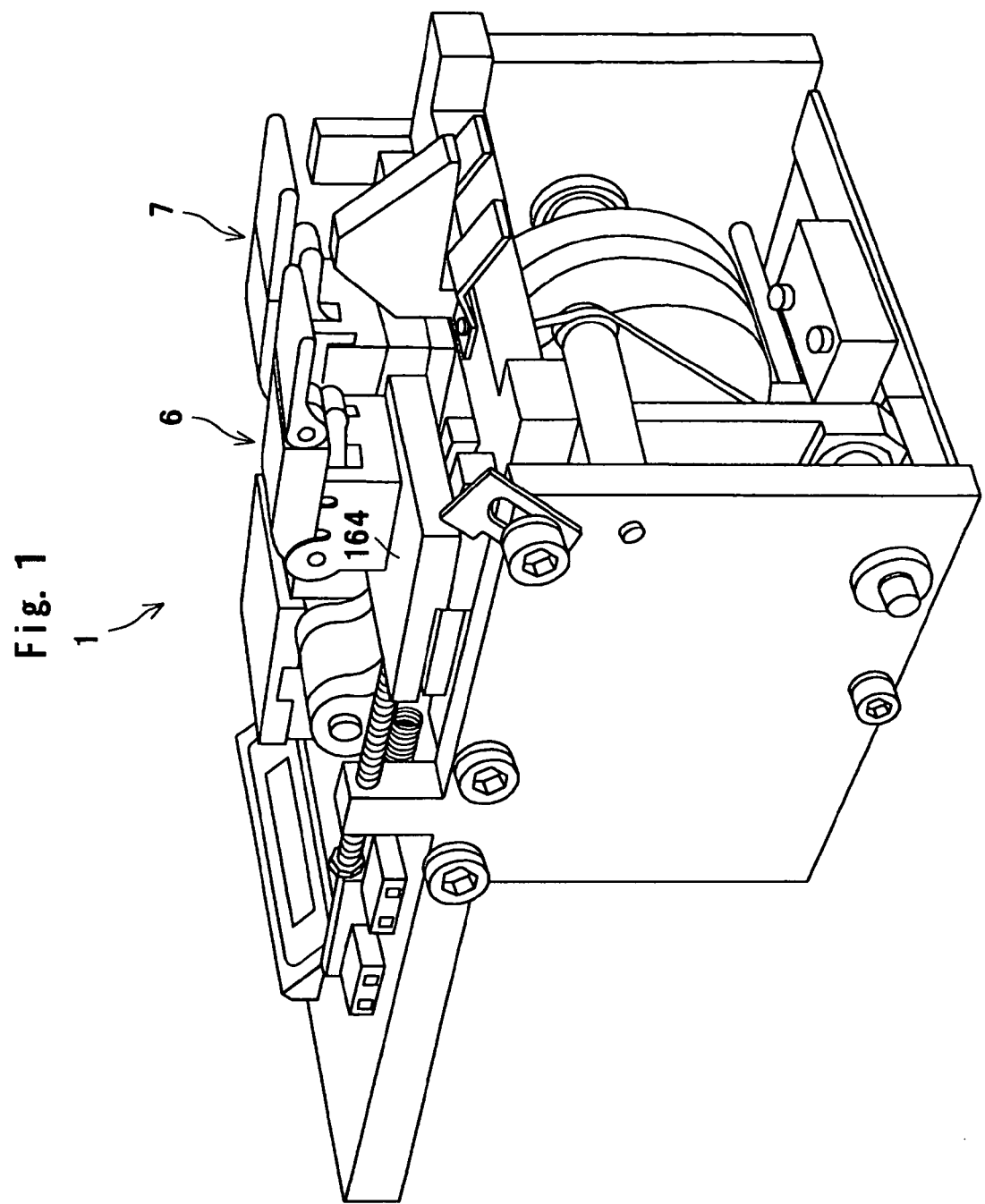
FIG. 1 is a schematic perspective view of a tube connecting apparatus in an embodiment to which the present invention is applicable.
Figure 2:
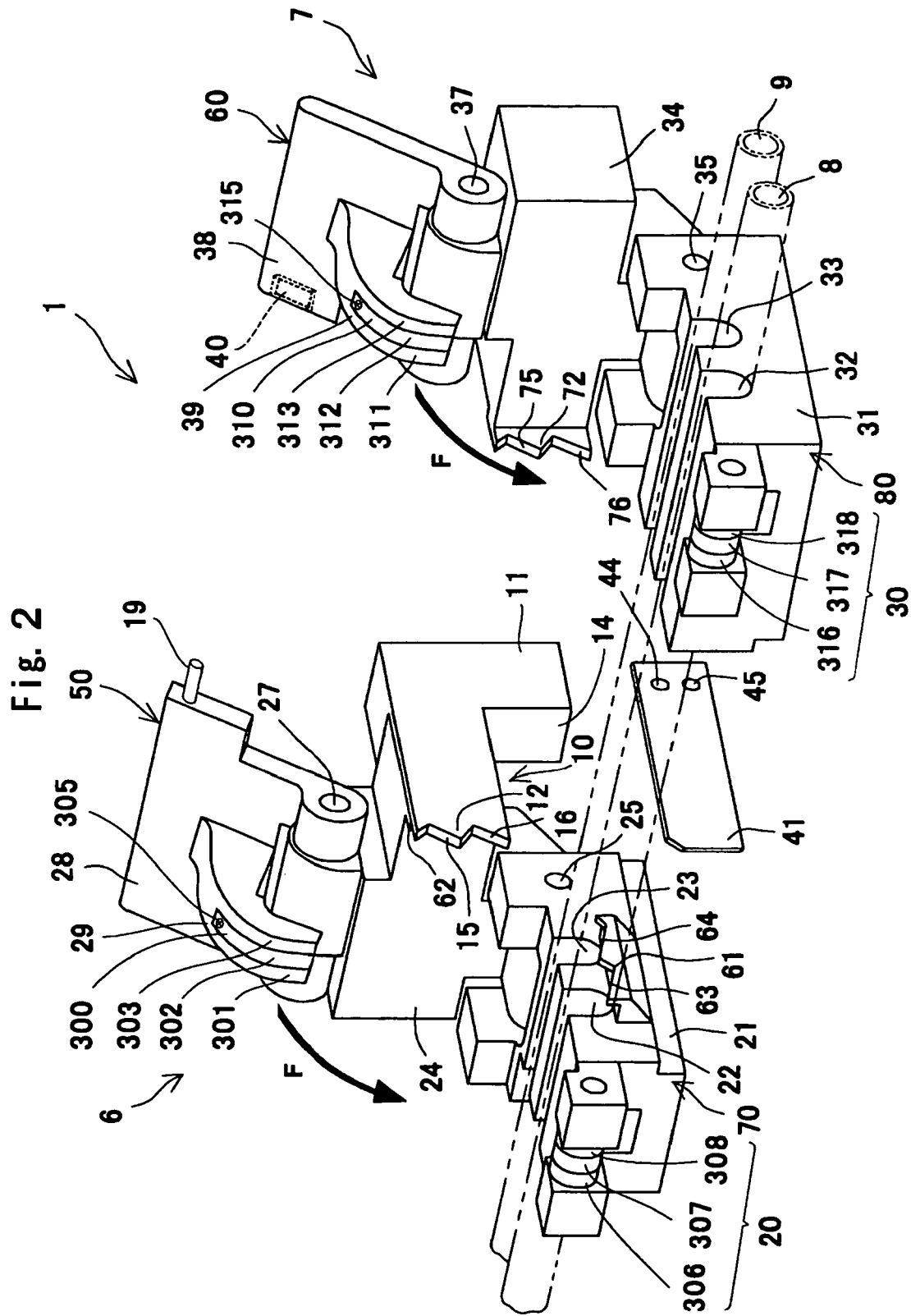
FIG. 2 is a perspective view showing clamps of the tube connecting apparatus.

As shown in FIG. 1 and FIG. 2, a tube connecting apparatus 1 of the present embodiment is equipped with a first clamp 6 serving as a tube clamp apparatus (a first holding section) and a second clamp 7 serving as a tube clamp apparatus (a second holding section), both of which hold two flexible tubes 8, 9 approximately in a parallel state, and a tube-pushing member 10 which is disposed between the first clamp 6 and second clamp 7 and adjacent to the first clamp 6 to press the tubes 8, 9 to a flat state. The tube connecting apparatus 1 is accommodated in an unillustrated casing such that protruded members as shown in FIG. 1 are hidden. (See FIG. 3.)

The first clamp 6 has a first lower jaw portion 70, which forms a lower jaw of the first clamp 6 at which the tubes 8, 9 are placed and which serves as a placement clamp section, and a first upper jaw portion 50, which forms a upper jaw of the first clamp 6, which is movable in a direction (a direction of an arrow F in FIG. 2) of pressing the tubes 8, 9 placed at the first lower jaw portion 70 and in a direction (a direction opposite to the arrow F in FIG. 2) of separating from the tubes 8, 9, which presses the tubes 8, 9 to a flat state and which serves as a movable clamp section. On the other hand, in the same manner as the first clamp 6, the second clamp 7 also has a second lower jaw portion 80 which forms a lower jaw of the second clamp 7 at which the tubes 8, 9 are placed and which serves as a placement clamp section, and a second upper jaw portion 60, which forms a upper jaw of the second clamp 7, which is movable in a direction (a direction of an arrow F in FIG. 2) of pressing the tubes 8, 9 placed at the second lower jaw portion 80 and in a direction (a direction opposite to the arrow F in FIG. 2) of separating from the tubes 8, 9, which presses the tubes 8, 9 to a flat state and which serves as a movable clamp section.

The tubes 8, 9 are made of soft resin such as, for example, soft polyvinyl chloride or the like and have flexibility, in which blood is contained and sealed. These tubes 8, 9 have approximately the same shape with respect to an inner diameter, an outer diameter and a length in a state before blood is contained and sealed. The first clamp 6 has a holder 21 for holding the tubes 8, 9 as a part of the first lower jaw portion 70, and a covering body 24 which is fitted pivotably to a rear end portion of the holder 21 through a hinge 25 for opening and closing as a part of the first upper jaw portion 50.

A pair of grooves 22, 23, which are parallel with each other, of which cross-section is shaped as a letter U, and into which the two tubes 8, 9 are put respectively, are formed in the holder 21. It is preferable that a width of the grooves 22, 23 is set to have the same or a smaller width as/than a diameter of the tubes 8, 9 in an inartificial state. An operator pushes the tubes 8, 9 into inner sides thereof (a downward direction in FIG. 2) to put the tubes 8, 9 into the grooves 22, 23. The covering body 24, in a closed state, covers the grooves 22, 23 and has a function for fixing the tubes 8, 9 such that the tubes 8, 9 are put inside the grooves 22, 23 so as not to get rid of the grooves 22, 23.

The first clamp 6 has a locking mechanism for retaining the covering body 24 in a closed state. The locking mechanism is constituted by a hook section 300 which is provided at a side of the first upper jaw portion 50 and which maintains a pressing state of the first upper jaw portion 50 against the tubes 8, 9, and a roller 20 which is provided at a side of the first lower jaw portion 70 to engage and stop the hook section 300 and which has a latch function.

The hook section 300 has a plate piece 28 which is fixed pivotably to a tip of the covering body 24 through a hinge 27, and a pawl member 29 which is formed to protrude toward an inner face of the plate piece 28. Incidentally, a shaft 19 which protrudes toward a side of the second clamp 7 from an end face of the plate piece 28 is fitted to the plate piece 28.

A tip portion of the pawl member 29, namely, a side thereof to engage the roller 20 is divided into plural members in a direction that the first upper jaw portion 50 presses the tubes placed at the first lower jaw portion 70, in other words, in a direction orthogonal to a longitudinal direction of the tubes 8, 9 placed at the first lower jaw portion 70. In this embodiment, the pawl member 29 is disposed so that a hook portion A 301, a hook portion B 302 and a hook portion C 303 are located in parallel. An inner side face (a face of a front side in FIG. 2) formed by these hook portions is arranged to have an approximately R shaped coplanar face. The hook portion A 301 and the hook portion C 303 are made of a unified material (stainless steel) which is integrated with a base portion of the pawl member 29.

Figure 12:
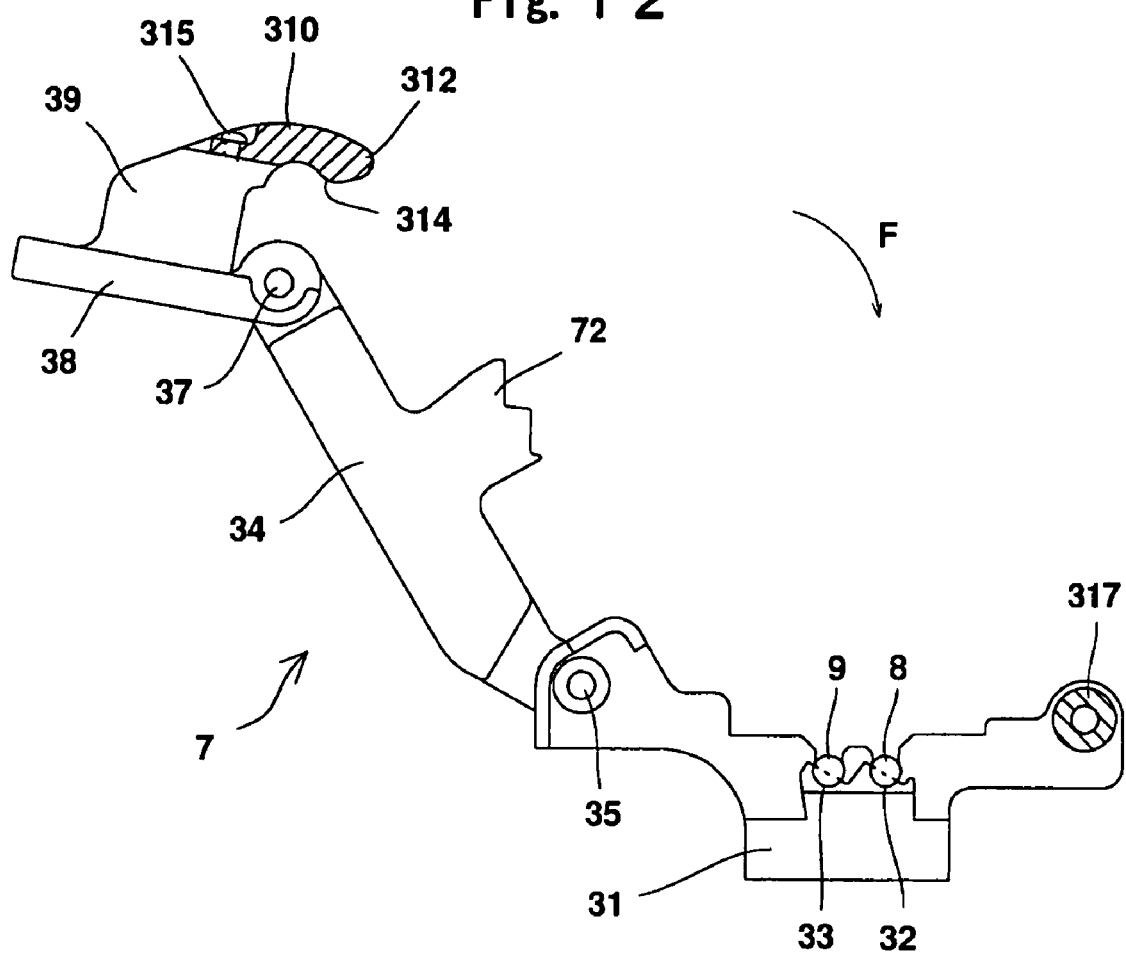
FIG. 12 is a side view in an opened state of a second clamp at which two tubes are placed.

In the hook portion B 302, which is sandwiched between the hook portion A 301 and the hook portion C 303 and which is disposed at a center of the hook portions, an unillustrated protruded portion 304 (the same shape as the protruded portion 314, See FIG. 12 to FIG. 14.), which maintains an engagement state with a roller B 307 that constitutes the roller 20 as stated later and that serves as an engagement member, which prevents the plate piece 28 locked by the locking mechanism from back-tracking (a movement in a direction opposite to the arrow F in FIG. 2), and which serves as a protruded portion, is formed at one side (a tip side) of the hook portion B 302 and an opposite face (rear face) side of an inner face of the hook portion B 302. The hook portion B 302 is made long in a direction opposite to tubes 8, 9 placed at the first lower jaw portion 70 and an end of another side thereof is fixed from an inner face side by a screw 305 so that the hook portion B 302 exhibits a function of a plate spring due to elastic deformation. In this embodiment, POM (polyoxymethylene=polyacetal resin) is used as a material for the hook portion B 302, and the hook portion B 302 is constituted by a resin member serving as an elastic member which has a flexure property of bending so as to change its self-shape or having elasticity according to external pressure.

Accordingly, the pawl member 29 is constituted by the base portion made of stainless steel, the hook portion A 301, the hook portion C 303, and the resin made hook portion B 302 having the flexure property and the end of another side thereof is fixed by the screw.

On the other hand, the roller 20 is constituted by a plurality of a rotatable roller A 306, a rotatable roller B 307 and a rotatable roller C 308 into which a shaft is inserted and of which diameters are approximately equal. The roller B 307 located at a center has a latch function for engaging the protruded portion 304 formed at one side of the hook portion B 302 and a slide face which is connected with the protruded portion 304. (See also FIG. 13 and FIG. 14.) A width of the roller B 307 is set almost equal to that of the hook portion B 302. In the same manner as the hook portion B 302, the POM is used as a material for the roller B 307. The roller A 306 and the roller C 308 adjacent to the roller B 307 are disposed so as to slide corresponding to the hook portion A 301 and the hook portion C 303 of the pawl member 29, respectively. In this embodiment, a stainless steel is used as a material for the roller A 306 and the roller C 308 in the same manner as the hook portion A 301, and the hook portion C 303.

In this embodiment, in order to secure locking operation according to the locking mechanism successively (to maintain pressing force to the tubes 8, 9 appropriately), reaction force at a time that the hook portion B 302 bends subject to external pressure, when the covering body 24 is closed by an operator to press the tubes 8, 9 to a flat state, is set to be smaller than pressing force that the pawl member 29 (hook portion A 301, hook portion B 302 and hook portion C 303) effects on the roller 20 (roller A 306, roller B 307 and roller C 308). Further, reaction force at a time that the hook portion B 302 bends subject to external pressure is set to be larger than or equal to load force of the roller B 307 against the protruded portion B 304. Accordingly, the hook portion B 302, among resins made of the POM, is set such that its flexure property satisfies the following equation (1).

Pressing Force at a time of locking>Reaction Force due to bending >=Load Force of roller B against protruded portion (1)

Accordingly, by pivoting the plate piece 28 in a direction of an arrow F in FIG. 2 to engage the pawl member 29 with the roller 20 in a state that the covering body 24 is closed, the covering body 24 is locked so as not to open. For this reason, difficulties in cutting and connecting of the tubes are prevented since the covering body 24 is prevented from being opened unexpectedly during connecting of the tubes, and accordingly fixing (holding) to the tubes 8, 9 as well as pressing according to the first clamp 6 and the second clamp 7 are not canceled.

A tube-pushing member 10 is connected with the first clamp 6 in a contact state at a side of the second clamp 7. The first clamp 6 has a saw-shaped pressure closing member 61 which is fixed to a side face of the holder 21, and a saw-shaped pressure closing member 62 which is fixed to a side face of the covering body 24 and which bites the pressure closing member 61 each other. The pressure closing member 61 has inclined faces 63, 64 at positions corresponding to the grooves 22, 23 respectively, while inclined faces 65, 66, which are parallel to the inclined faces 63, 64 respectively and which are disposed at positions having a predetermined distance from the inclined faces 63, 64, are formed at the pressure closing member 62. (See FIG. 11.) Accordingly, when the covering body 24 is closed in a state that the tubes 8, 9 are put in the grooves 22, 23, the tube 8 is pressed by the inclined faces 63, 65 and the tube 9 is pressed by the inclined faces 64, 66 since the pressure closing members 61, 62 engage (bite) each other. According to the structure of the first clamp 6, dislocation (offset) or deformation of the tubes 8, 9 is restrained and easy and proper connection is secured when cut faces of the tubes 8, 9 are connected with each other, which will be stated later.

On the other hand, the second clamp 7 is disposed at a side of the first clamp 6 and adjacent to the first clamp 6 via the tube-pushing member 10. The second clamp 7, in the same manner as the first clamp 6, has a holder 31 at which a pair of grooves 32, 33 are formed and which holds the tubes 8, 9, a covering body 34 which pivots to the holder 31 for opening and closing, and a locking mechanism. A structure thereof corresponds to the first clamp 6. Incidentally, a long hole 40 into which the shaft 19 can be inserted is formed at an end face of the plate piece 38 facing a side of the first clamp 6. The long hole 40 has a function for allowing the shaft 19 to move when the first clamp 6 moves in tube connecting operation as stated later.

A locking mechanism of the second clamp 7 will be explained in detail. The locking mechanism, in the same manner as the locking mechanism of the first clamp 6, is constituted by a hook section 310 which is provided at a side of the second upper jaw portion 60 and which maintains a pressing state of the second upper jaw portion 60 against the tubes 8, 9, and a roller 30 which is provided at a side of the second lower jaw portion 80 to engage and stop the hook section 310 and which has a latch function.

The hook section 310 has a plate piece 38 which is fixed pivotably to a tip of the covering body 34 through a hinge 37, and a pawl member 39 which is formed to protrude toward an inner face of the plate piece 38. A tip portion of the pawl member 39 is divided into plural members along a longitudinal direction of the tubes 8, 9 placed at the second lower jaw portion 80. In this embodiment, the pawl member 39 is disposed so that a hook portion A 311, a hook portion B 312 and a hook portion C 313 are located in parallel. An inner side face formed by these hook portions is arranged to have an approximately R shaped coplanar face. Further, the hook portion A 311 and the hook portion C 313 are made of a stainless steel which is integrated with a base portion of the pawl member 39.

A protruded portion 314 (See FIG. 12 to 14.), which maintains an engagement state with a roller B 317 that constitutes the roller 30 and that serves as an engagement member, which prevents the plate piece 38 locked by the locking mechanism from back-tracking and which serves as a protruded portion, is formed at the hook portion B 312 disposed at a center of the hook portions. Further, the hook portion B 312 is made long in a direction opposite to tubes 8, 9 placed at the second lower jaw portion 80 and an end of another side thereof is fixed from an inner face side by a screw 315 so that the hook portion B 312 exhibits a function of a plate spring due to elastic deformation. In this embodiment, the POM is used as a material for the hook portion B 312, and the hook portion B 312 is constituted by a resin member serving as an elastic member which has a flexure property of bending so as to change its self-shape or having elasticity according to external pressure.

On the other hand, the roller 30 is constituted by a plurality of a rotatable roller A 316, a rotatable roller B 317 and a rotatable roller C 318 into which a shaft is inserted and of which diameters are approximately equal. The roller B 317 located at a center has a function for engaging the protruded portion 314 formed at one side of the hook portion B 312 and a slide face which is connected with the protruded portion 314. (See FIG. 13 and FIG. 14.) A width of the roller B 317 is set almost equal to that of the hook portion B 312. The roller A 316 and the roller C 318 adjacent to the roller B 317 are disposed so as to slide corresponding to the hook portion A 311 and the hook portion C 313 of the pawl member 39, respectively. In this embodiment, a stainless steel is used as a material for the roller A 316 and the roller C 318 in the same manner as the hook portion A 311 and the hook portion C 313.

Further, in this embodiment, in order to secure locking operation according to the locking mechanism successively, reaction force at a time that the hook portion B 312 bends subject to external pressure, when the covering body 34 is closed by an operator to press the tubes 8, 9 to a flat state, is set to be smaller than pressing force that the pawl member 39 effects on the roller 30. Further, reaction force at a time that the hook portion B 312 bends subject to external pressure is set to be larger than or equal to load force of the roller B 317 against the protruded portion 314. Accordingly, the hook portion B 312 is also set such that its flexure property satisfies the above stated equation (1).

The second clamp 7 has a saw-shaped pressure closing member 71 (unillustrated) which is fixed to a side face of the holder 31 and at a side of the holder 21, and a saw-shaped pressure closing member 72 which is fixed to a side face of the covering body 34 and at a side of the covering body 24 and which bites the pressure closing member 71 each other. The pressure closing member 71 has inclined faces 73, 74 at positions corresponding to the grooves 32, 33, respectively (See FIG. 11.) Inclined faces 75, 76, which are parallel to the inclined faces 73, 74 respectively and which are disposed at positions having a predetermined distance from the inclined faces 73, 74, are formed at the pressure closing member 72.

The first clamp 6 and the second clamp 7 are usually located such that the grooves 22, 32 correspond to (align) the grooves 23, 33 respectively each other.

The tube-pushing member 10 is disposed movably and integrally with the first clamp 6. Further, the tube-pushing member 10 has a saw-shaped tip portion 12 (corresponding to the pressure closing members 62, 72) at which inclined faces 15, 16 are formed in the same manner as the first clamp 6 and the second clamp 7. However, it differs from the first clamp 6 and the second clamp 7 in that it does not have the pressure closing members 61, 71 which bite each other via the tubes 8, 9. Furthermore, the tip portion 12 of the tube-pushing member 10 is placed at a position protruded a little more than a position of the pressure closing member 62 of the first clamp 6, although the tip portion 12 has the same saw shape as the pressure closing member 62 of the first clamp 6 and the pressure closing member 72 of the second clamp 7.

A supporting member 11 having a L shaped cross section is fixed to the tube-pushing member 10 by screws. The supporting member 11 has a supporting member projection portion 14 which projects downward. An unillustrated U shaped slider is provided at the supporting member 11. This slider is allowed to move along an unillustrated rail. The unillustrated rail is fixed to a rail supporting member (unillustrated) and the rail supporting member is fixed to the covering body 24 by screws. For this reason, the tube-pushing member 10 is integrated with the first clamp 6 and can move relatively to the first clamp 6. Incidentally, since the tip portion 12 of the tube-pushing member 10 is protruded more than the pressure closing member 62 of the first clamp 6, the tip portion 12 pushes the tubes 8, 9 prior to the first clamp 6 when the covering body 24 is closed.

Figure 3:
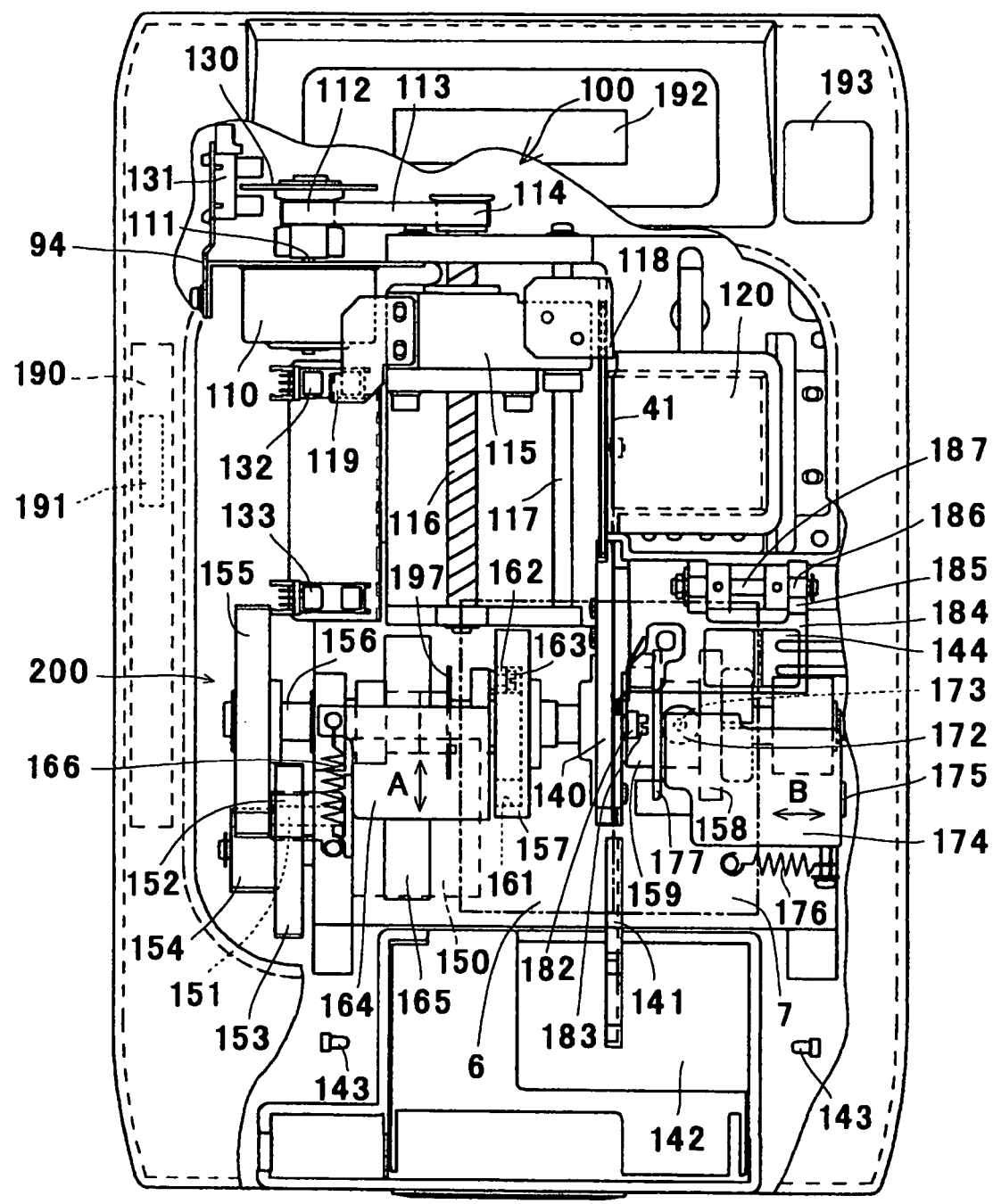
FIG. 3 is a partially broken plan view of the tube connecting apparatus.

Further, as shown in FIG. 3, the tube connecting apparatus 1 is equipped with a wafer feeding mechanism 100 which feeds the wafer (cutting plate).

A fitting member 94 is set up at the casing of the tube connecting apparatus 1 and a pulse motor 110 capable of normal and reverse rotation is fixed by screws to the fitting member 94. A gear 112 is fixed to an output shaft 111 of the pulse motor 110, and a timing belt 113 is entrained between the gear 112 and a gear 114. The gear 114 is disposed at an axis of a ball screw 116 on which a wafer feeding member 115 that feeds the wafer 41 capable of cutting the tubes 8, 9 one by one is provided and that is called as a shuttle. An unillustrated nut which engages the ball screw 116 is provided at an interior of the wafer feeding member 115. The wafer feeding member 115 moves along the ball screw 116 due to rotation of the ball screw 116 in accordance with rotation of the gear 114 of which driving source is the pulse motor 110. One side of the wafer feeding member 115 is supported by a rod-shaped shaft 117 to stabilize posture (movement) of the wafer feeding member 115 at the time of feeding the wafer. A feeding piece 118 which feeds the wafer 41 accommodated in a wafer cassette 120 which accommodates a plurality of wafers 41 (70 pieces in this embodiment) one by one from the wafer cassette 120 in accordance with movement of the wafer feeding member 115 is fixed at an end portion of the wafer feeding member 115.

Unillustrated compression springs are disposed at an interior of the wafer cassette 120 so as to energize the wafers 41. When the wafer 41 is fed by the feeding piece 118 of the wafer feeding member 115, an adjacent wafer faces a side of the wafer feeding member 115 one after another, which allows the feeding piece 118 to feed the wafer 41 continuously. Incidentally, the wafer feeding member 115 can move in a direction opposite to a direction of feeding the wafer 41 according to reverse rotation of the pulse motor 110.

The wafer 41 is a self-heating typed heat cutting plate. For example, a sheet of a metal plate such as a copper plate or the like is folded into two, and a resistance body having a desired pattern for heating is formed inside the folded metal plate via insulating layers to manufacture the wafer. The wafer 41 has a structure that terminals 44, 45 (See FIG. 2.) disposed at both ends of the resistance body are exposed at apertures formed at each end portion of the metal plate.

Further, a revolving plate 130 which is adjacent to the gear 112 and which has a plurality of slits and which rotates according to rotation of the pulse motor 110 is fixed to an end portion of the output shaft 111 of the pulse motor 110. The revolving plate 130 is provided to detect a moving amount of the wafer feeding member 115. At the vicinity of the revolving plate 130, a transmission type sensor 131 which detects a revolving amount of the revolving plate 130 is fixed by screws to the fitting member 94 at an opposite side of the gear 114 so as to stride the revolving plate 130.

A transmission type sensor 132 which detects the wafer feeding member 115 which is located at a feeding start position of the wafer 41 and a transmission type sensor 133 which detects the wafer feeding member 115 which is located at a feeding end position of the wafer 41 are disposed separately with a predetermined interval at an opposite side of the wafer cassette 120 via the ball screw 116. A piece to be detected 119 having an approximately L shape is fixed to the wafer feeding member 115 at an opposite side of the feeding piece 118. Incidentally, detection of the moving amount of the wafer feeding member 115 according to the above stated revolving plate 130 and the transmission type sensor 131 is carried out at an interval between both positions of the transmission type sensors 132, 133.

Figure 4:
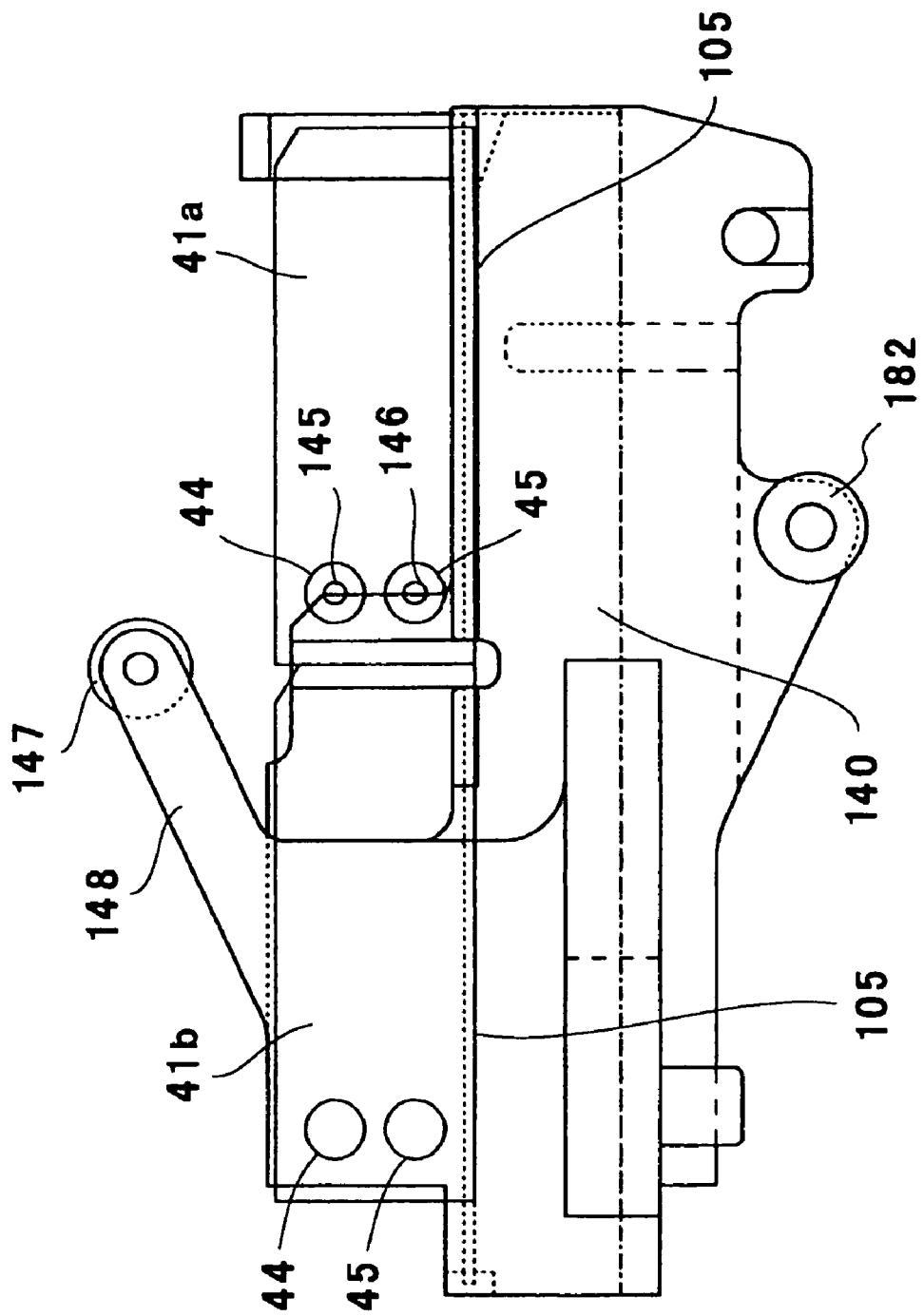
FIG. 4 is an enlarged side view of a wafer holder.

The wafer 41 fed by the wafer feeding member 115 is located to a downstream side of a wafer conveying path from the wafer cassette 120, then located inside the wafer holder 140 which holds the wafer 41 and which constitutes a part of a cutting unit. As shown in FIG. 4, in this embodiment, a structure that two pieces of the wafer 41 are held in the wafer holder 140 such that end faces thereof contact each other is employed, and the wafer 41 is supplied in a manner that a wafer 41a fed formerly from the wafer cassette 120 is pushed and moved on a conveying path 105 in the wafer holder 140 by a wafer 41b fed newly from the wafer cassette 120. In other words, the wafer 41b pushes and advances the wafer 41a forward, and the wafer 41a is located at a position for cutting the tubes 8, 9 in the wafer holder 140.

The terminals 44, 45 for the wafer 41a which is located at a forward side in the wafer holder 140 are supplied with electricity by projection-shaped electrode portions 145, 146 from an unillustrated power unit via a harness of which illustration is omitted. The electrode portions 145, 146 are fixed integrally to the wafer holder 140 and are disposed so as to face via the wafer 41 to an end surface of one wall side (a back side in FIG. 4) of the wafer holder 140. Incidentally, as stated later, because the wafer holder 140 moves up and down (swings) at the time of cutting the tubes 8, 9, the electrode portions 145, 146 integrally fixed to the wafer holder 140 also have a structure capable of supplying electricity for heating to the wafer 41.

The resistance body inside the wafer 41 generates heat according to electricity supply from the electrode portions 145, 146, and the wafer 41 is heated up to the temperature (ex. approximately 260 to 320 deg. C.) capable of melting and cutting the tubes 8, 9. Further, because it is preferable that the wafer 41 is disposable (for single use) at every connecting operation of the tubes, the wafer feeding mechanism 100 has a structure capable of exchanging the wafer 41 held in the wafer holder 140 every time the tubes 8, 9 are connected.

The wafer holder 140 is heated by a heater 144 which is fitted to a pivot-supporting plate 184 which will be stated later. (See FIG. 3.) While electric power is supplied to the heater 144 from the unillustrated power unit, the wafer holder 140 always keeps a heated state during a period that electric power is supplied to the tube connecting apparatus 1. An unillustrated temperature sensor such as a thermistor or the like which detects a temperature of the wafer holder 140 is fixed to the wafer holder 140, and the wafer holder 140 is controlled to keep a predetermined temperature (70 deg. C. in this embodiment).

Temperature controlling in this embodiment will be explained further. Since a surface of the wafer 41 is covered by the copper plate as stated above, the wafer 41 is influenced by the temperature that the wafer holder 140 has due to the material (copper) characteristics when it is inserted into the wafer holder 140 and it reaches the predetermined temperature immediately after it is inserted into the wafer holder 140. A controlling unit 190 as stated later forecasts that the wafer 41 supplied electric power from the electrode portions 145, 146 reaches a predetermined temperature (ex. about 260 to 320 deg. C. as stated above) after a predetermined period of time from a time that the wafer 41 is inserted into the wafer holder 140 in order to shift to tube-cutting operation according to the wafer 41 (ascending movement of the wafer holder 140).

Figure 5:
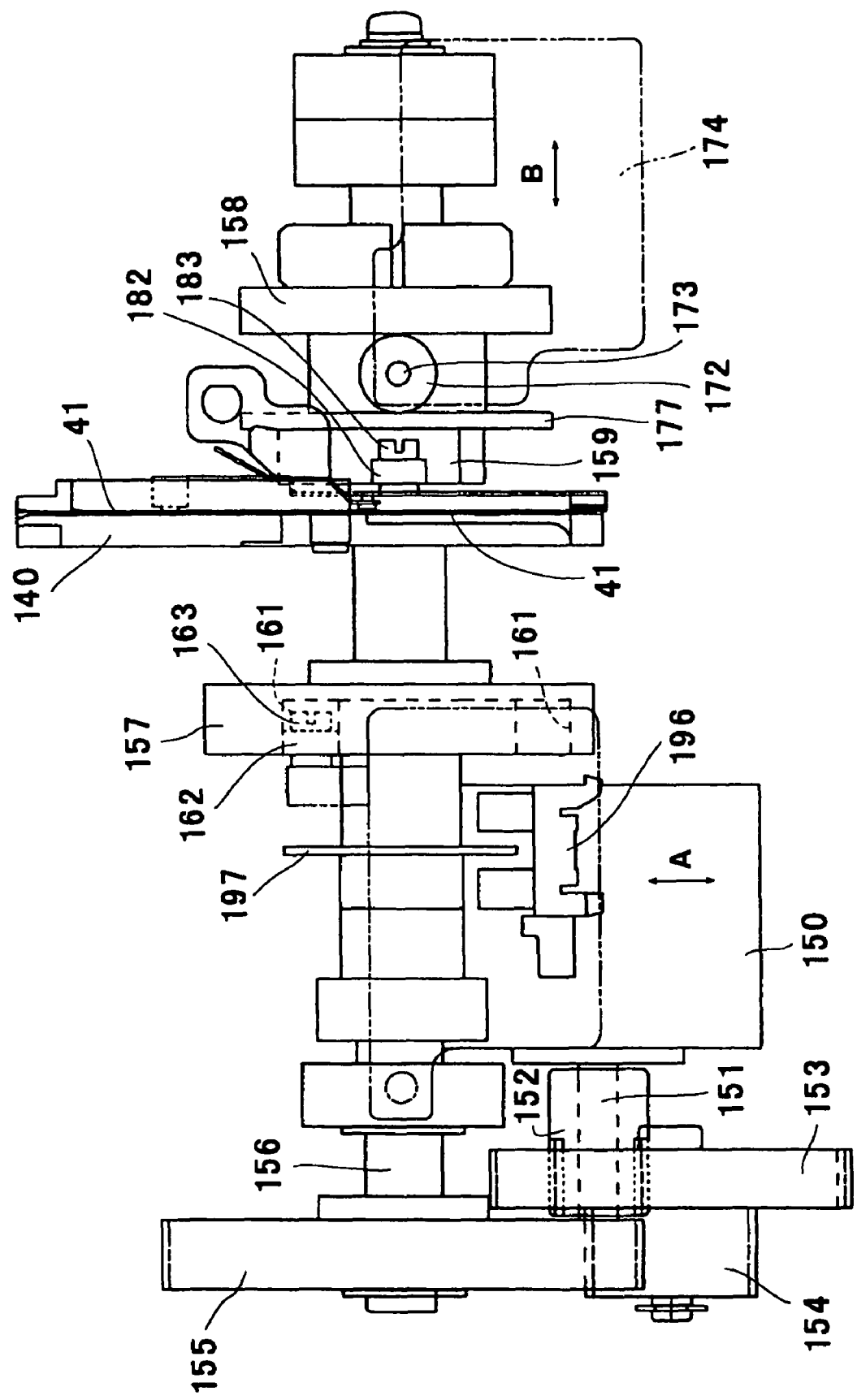
FIG. 5 is an enlarged plan view of a drive-conveying mechanism.

As shown in FIG. 3 and FIG. 5, the tube connecting apparatus 1 is equipped with a drive-conveying mechanism 200 that functions as a movement unit which moves the first clamp 6 and the second clamp 7 and that moves the wafer holder 140 (up and down).

A pulse motor 150 which is a driving source of the drive-conveying mechanism 200 and which is capable of normal and reverse rotation is fitted by screws to an unillustrated motor fitting member which is fixed to the casing of the tube connecting apparatus 1 at a side of the wafer holder 140 and at a downstream side of the wafer feeding member 115. A gear 152 is fixed to an output shaft 151 of the pulse motor 150 and the gear 152 bites a gear 153 each other. A gear 154 is fixed on a coaxial line of the gear 153 and this gear 154 bites a gear 155 each other. A driving shaft 156 which rotates together with the gear 155 according to driving force conveyed to the gear 155 is provided at a center of rotation for the gear 155. A cam 157 which regulates movement of the first clamp 6, a cam 158 which regulates movement of the second clamp 7 and a cam 159 which regulates movement of the wafer holder 140 are respectively fixed on the driving shaft 156. Accordingly, driving force from the pulse motor 150 is conveyed to the driving shaft 156 and the cams 157, 158 and 159 are driven to rotate respectively.

A groove 161 is formed at an interior of the cam 157, and a bearing 162 which engages an edge face of the groove 161 is connected via a fitting member 163 to a supporting table 164 (See FIG. 1.) which supports the first clamp 6 in a fixed state. For this reason, the bearing 162 slides along the edge face of the groove 161 formed at the interior of the cam 157 to enable the first clamp 6 to move in a predetermined direction (a direction of an arrow A in FIG. 3). Incidentally, a liner guide 165 which guides the supporting table 164 (the first clamp 6) so as to move stably is disposed at a bottom portion of the supporting table 164 in a contact state. Further, a compression spring 166 is bridged at one end of the supporting table 164 so as to energize this supporting table 164 to a predetermined direction.

On the other hand, a bearing 172 which engages a surface of the cam 158 is connected via a fitting member 173 to a supporting table 174 which supports the second clamp 7 in a fixed state. For this reason, according to rotation of the cam 158, the bearing 172 slides along the surface of the cam 158 to enable the second clamp 7 to move in a predetermined direction (a direction of an arrow B in FIG. 3). Incidentally, in this embodiment, the bearing 172 is constituted to not only engage a side face of the cam 158 but also engage a surface of a flange portion 177 which is integrally formed with the cam 159 which regulates the movement of the wafer holder 140. In short, the bearing 172 is located between the side face of the cam 158 and the flange portion 177 so that the bearing 172 has a structure capable of engaging and sliding on both of them, and the flange portion 177 is included in a part of a function of the cam 158 which regulates the movement of the second clamp 7. A notched portion 178 (See FIGS. 15(C) and (D).) is formed at a part of the cam 158 as stated later. Incidentally, a liner guide 175 which guides the supporting table 174 (the second clamp 7) so as to move stably is disposed at a bottom portion of the supporting table 174 in a contact state. Further, a compression spring 176 is bridged at one end of the supporting table 174 so as to energize this supporting table 174 to a predetermined direction.

Further, a bearing 182 (See FIG. 4.) is fitted via a fitting member 183 to a bottom portion of the wafer holder 140. Because the bearing 182 slides along a surface shape of the cam 159 according to rotation of the cam 159, the wafer holder 140 is constituted so as to move in a predetermined direction (a vertical direction). In other words, by pivoting integrally with and around a shaft axis 187 which penetrates a hole 186 formed at a protruded portion 185 of the pivot-supporting plate 184 which is fitted to the wafer holder 140, the wafer holder 140 is structured so as to be able to swing in a vertical direction. A slanted projection portion 148 which has a metal roller 147 at its tip is integrally formed with an upper side of the wafer holder 140 (See FIG. 4.), and the roller 147 is brought to contact the supporting member projection portion 14 (See FIG. 2.). Due to a change in the surface shape of the cam 159, when the wafer holder 140 ascends (swings) at a predetermined timing, the tube-pushing member 10 (See FIG. 2.) is pushed upward. Thus, the projection portion 148 has a function for guiding the tube-pushing member 10 to the evacuating position.

Figure 6:
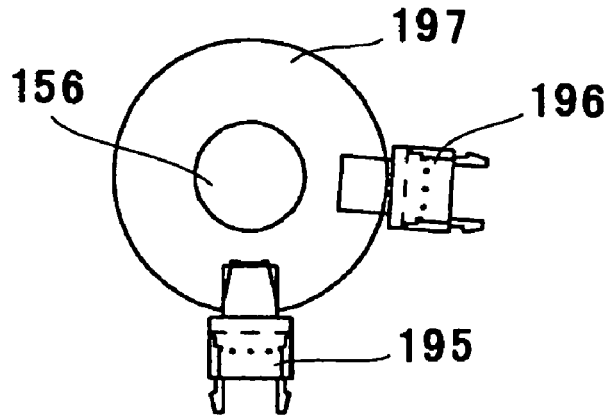
FIG. 6 is a side view showing a revolving plate fitted to a driving shaft and transmission type sensors.
Figure 6:
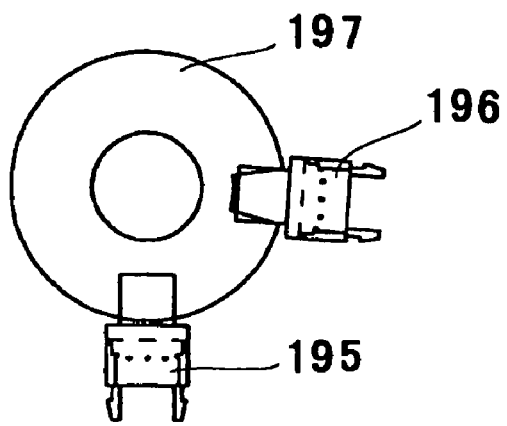
Figure 6:
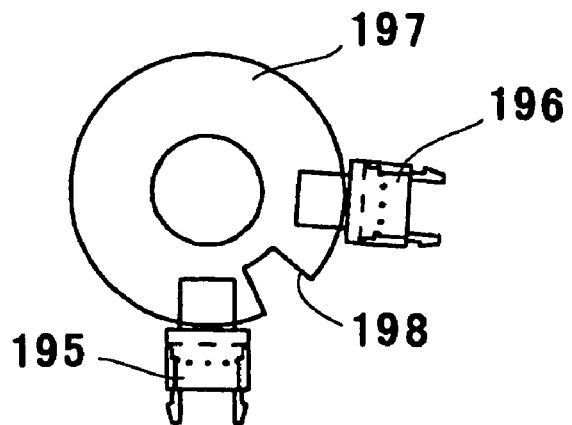

Further, a revolving plate 197 at which a notch 198 is formed is fixed to the driving shaft 156 between the cam 157 and the gear 155. (See FIG. 6.) Transmission type sensors 195, 196 are disposed adjacent to the revolving plate 197 so as to stride the revolving plate 197. By utilizing the notch 198 formed at the revolving plate 197, position detection for the first clamp 6 and the second clamp 7 is carried out by the transmission type sensors 195 and 196. Namely, while the revolving plate 197 rotates in a predetermined direction according to rotation of the driving shaft 156, when light from the transmission type sensor 195 transmits the notch 198 (See FIG. 6(A).), the first clamp 6 and the second clamp 7 are defined at their initial positions. Namely, the transmission type sensor 195 is used as a sensor for detecting the initial positions of the first clamp 6 and the second clamp 7.

As shown in FIG. 3, a guide 141 which guides (constitutes the conveying path for) a used wafer 41 and a waste box 142 which accommodates the used wafer(s) 41 are disposed at a downstream side of the wafer holder 140. The wafer 41 located at a position at which it can cut the tubes is wasted (accommodated) to the waste box 142 after cutting and connecting operation of the tubes 8, 9 is carried out. This wasting operation is also carried out by pushing the end faces of the wafers 41 each other as stated above. The wasted wafer 41 is guided along the guide 141 and then dropped into the waste box 142 to accommodate it. A transmission type sensor 143 which detects a full state of the used wafers 41 wasted and accommodated in the waste box 142 is disposed at a side of the waste box 142 and at a position having a predetermined height from a bottom of the waste box 142.

Furthermore, the tube connecting apparatus 1 is equipped with a controlling unit 190 for carrying out movement controlling of whole of the apparatus, a display panel 192 for displaying a state of the apparatus to an operator, a start button 193 for starting movement/operation of the apparatus, a constant voltage power supply unit which converts commercial AC power source to DC power source which can drive/actuate actuators such as pulse motors and the like as well as the controlling unit 190.

The controlling unit 190 is constituted with a CPU 191 which operates at a high clock speed as a central processing unit, a ROM in which controlling program and controlling data for the tube connecting apparatus 1 are memorized, a RAM which works as a work area for the CPU 191 and an internal bus which connects these. An external bus is connected to the controlling unit 190. A display controlling section which controls display of the display panel 192, a start button controlling section which controls a start command from the start button 193, a sensor controlling section which controls signals from various sensors such as transmission type sensors, temperature sensors and the like, an actuator controlling section which controls motor drivers which sends driving pulses to pulse motors are connected to the external bus. Incidentally, the display panel 192, the start button 193, the above-stated various sensors, the pulse motors 110, 150 are connected respectively to the display controlling section, the start button controlling section, the sensor controlling section and the actuator controlling section.

(Operation)

Next, operation of the tube connecting apparatus 1 in this embodiment will be explained in the order of clamping operation with respect to pressing and maintaining pressing thereof against the tubes 8, 9, cutting and connecting routine carried out by the CPU 191 in the controlling unit 190. Incidentally, in order to simplify an explanation, the second clamp 7 is represented to explain the clamping operation.

<Clamping Operation>

Prior to tube cutting and connection operation (execution of the cutting and connecting routine by the CPU 191) due to the tube connecting apparatus 1, an operator pushes the tubes 8, 9 to the grooves 32, 33 formed at the holder 31. Thus, the tubes 8, 9 are put (placed) inside the grooves 32, 33. (A state shown in FIG. 12) In this state, the tubes 8, 9 has an original cylindrical shape (circular cross sectional shape in figures) because of before starting pressing operation to the tubes 8, 9.

Figure 13A:
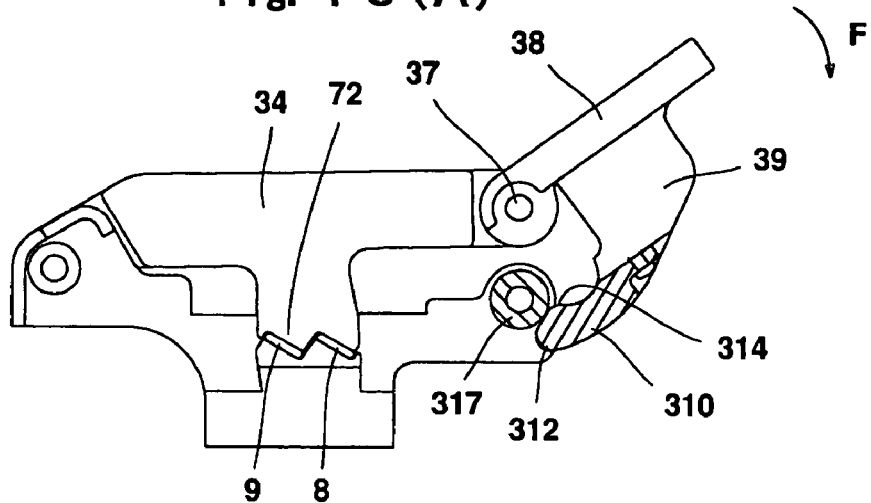
FIG. 13 is a side view showing operation of a locking mechanism of the second clamp in which a hook portion B and a roller B are expressed in cross section, FIG. 13(A) showing clamping operation 1, FIG. 13(B) showing clamping operation 2 and FIG. 13(C) showing a state that locking according to the locking mechanism is completed.
Figure 13B:
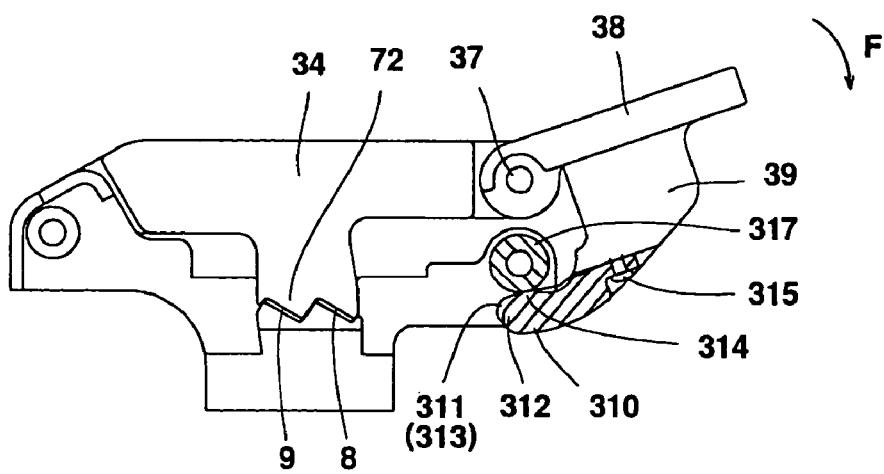
Figure 14A:
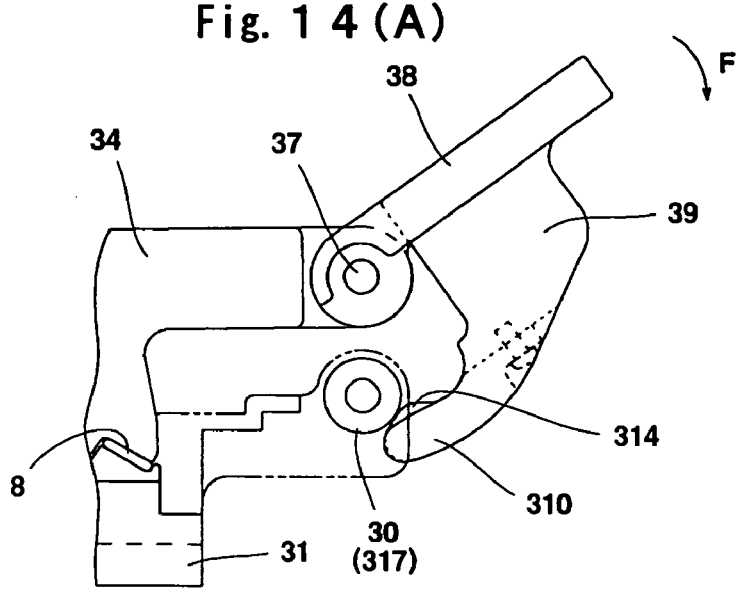
FIG. 14 is a side view showing operation of the locking mechanism of the second clamp, FIG. 14(A) showing the clamping operation 1, FIG. 14(B) showing the clamping operation 2 and FIG. 14(C) showing the state that locking according to the locking mechanism is completed.
Figure 14B:
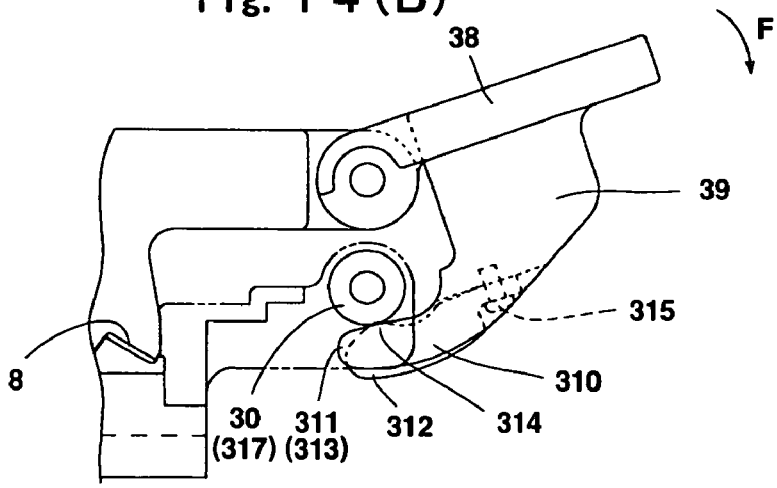

Next, an operator grasps the tip portion of the plate piece 38 provided pivotably at one end portion of the covering body 34 through the hinge 37 to push and move the pawl member 39 downward a side of the holder 31 (a direction of an arrow F in FIG. 12) so that the saw-shaped pressure closing member 72 abuts the tubes 8, 9 for pressing operation. Thereby, after the pressure closing member 72 abuts the tubes 8, 9, the pawl member 39 pivots around the hinge 37 in the direction of the arrow F, then the tip portion of the pawl member 39 shifts to a state that it collides with the roller 30. (A state shown in FIGS. 13(A) and FIG. 14(A)) Since, in this state, the pressure closing member 72 pushes the tubes 8, 9 to some degree, the tubes 8, 9 shifts to a deformed state from the cylindrical shape shown in FIG. 12. Incidentally, in FIG. 13(A), in order to characterize structural portions relating to the present invention, the hook portion B 312 having the protruded portion 314 at the tip of the pawl member 39 and the roller B 317 having an engagement relationship with the protruded portion 314 are illustrated by a partial cross section with diagonal lines. As shown in FIG. 13(A), in this state, the protruded portion 314 of the hook portion B 312 made of the POM abuts the roller B 317.

When an operator, from this state, further pushes down the covering body 38 in a direction of the arrow F, the protruded portion 314 disposed at one side end portion of the hook portion B 312 advances toward a direction of a predetermined locking position in accordance with rotation of the roller B 317 with which the protruded portion 314 has an engagement relationship (the hook portion B 312 advances forward) to be pushed downward around another side which is fixed by screws as a fulcrum. In short, the hook portion B 312 having the flexure property yields to pressure caused by engagement with the resin made roller B 317 and it becomes a bending state. (A state shown in FIGS. 13(B) and FIG. 14(B)) In this state, a top part of the protruded portion 314 still has an engagement (contact) relationship with the roller B 317, yet, since the top part takes approximately the same face as upper faces of the adjacent hook portion A 311 and the adjacent hook portion C 313, the upper faces of the hook portion A 311 and the hook portion C 313 also slide to contact respectively circumferential surfaces of metal made rollers of the roller A 316 and the roller C 318 which are adjacent to the roller B 317 on both sides.

When an operator continues to pushes down the covering body 38 in a direction of the arrow F, in a state that all faces in a width direction of the hook section 310 at a side of engaging the roller 30 (the protruded portion 314, upper faces of the adjacent hook portions A 311 and C 313) slide to contact the roller 30 (resin made roller B 317, metal made rollers A 316, C 318 adjacent thereto on both sides) as stated above, the protruded portion 314 of the hook portion B 312 slides to contact the circumferential surface of the roller B 317 and the upper portions of the adjacent hook portion A 311 and the hook portion C 313 slide to contact circumferential surface of the roller A 316 and the roller C 318, then the protruded portion 314 is located at a predetermined locking position (an engagement maintaining position for maintaining engagement). (A state shown in FIGS. 13(C) and FIG. 14(C)) The roller B 317 of the roller 30 climbs over the protruded portion 314 of the hook portion B 312 so that the protruded portion 314 can advance to a direction of the locking position, and during this period of time, namely during a period shifted from a state shown in FIG. 13(B) to a state shown in FIG. 13(C), and from a state shown in FIG. 14(B) to a state shown in FIG. 14(C), a bending state of the hook portion B 312 is recovered to go back to an original state thereof.

In this state, the back-tracking of the plate piece 38 is prevented because the protruded portion 314 is retained at the predetermined locking position according to interaction among the pressing force, the reaction force and the load force, and the tubes 8, 9 are maintained in a predetermined pressing state by the pressure closing member 72 to retain the tubes 8, 9 in an expected flat state because the upper face portions of the hook portions A 311 and C 313 maintain the engagement relationship with the circumferential surfaces of metal-made rollers A 316 and C 318 and because of the hook function of the pawl member 39, in other words, because the locking function according to the locking mechanism is maintained.

Incidentally, in the above clamping operation, the second clamp 7 were exemplified, however, the same thing is also true to the first clamp 6.

<Cutting and Connecting Routine>

When power source is inputted to the controlling unit 190 via an unillustrated switch, the CPU 191 carries out initial setting process which reads out the controlling program and the controlling data from the ROM and develops them at the RAM.

Then, as shown in FIG. 6(A), the CPU 191 determines as to whether or not the transmission type sensor 195 detected the notch 198 in order to judge whether or not the first clamp 6 and the second clamp 7 are located at the initial positions (positions where the clamps can hold the tubes 8, 9 in the grooves 22, 23, 32, 33 in a parallel state each other). If a negative judgment is made, since the first clamp 6 and the second clamp 7 are not in the initial positions and can not secure regular cutting and connecting operation, the CPU 191 makes the display panel 192 via the display controlling section to display that an unillustrated reset button be pushed. When the unillustrated reset button is pushed, the CPU 191 drives the pulse motor 150 via the actuator controlling section in order to locate the first clamp 6 and the second clamp 7 at the initial positions. If an affirmative judgment is made (or the first clamp 6 and the second clamp 7 are located at the initial positions), the CPU 191 judges whether or not the waste box 142 is full according to a two-level signal from the transmission sensor 143. When an affirmative judgment is made, because the waste box 142 in which the wafers 41 wasted and accommodated is full and it is impossible for the wafer feeding mechanism 100 to feed the wafer 41 from the wafer cassette 120, the CPU 191 makes the display panel 192 to display that the waste box 142 is full and waits until a judgment that the waste box 142 is full is denied according to the signal from the transmission sensor 143. If a negative judgment is made, because it is capable of carrying out regular cutting and connecting operation to the tubes 8, 9, the CPU 191 makes the display panel 192 to display that putting (setting) of tubes 8, 9 is urged and waits until the start button 193 is pushed.

Figure 7:
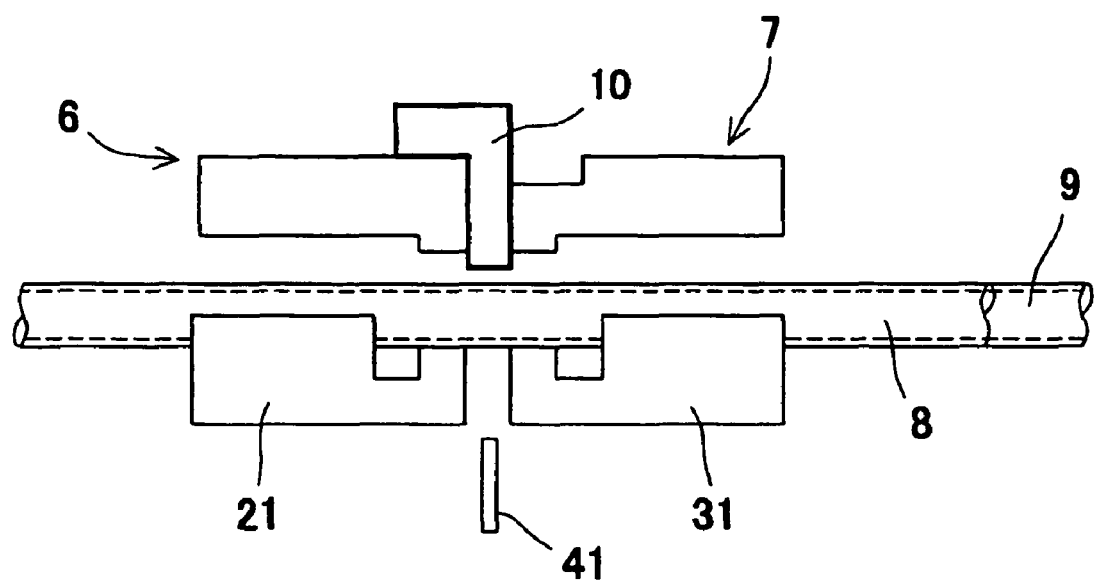
FIG. 7 is an explanatory drawing showing operation 1 of main portions of the tube connecting apparatus and a front view illustratively showing a state that covering bodies of a first clamp and a second clamp begin to be closed.
Figure 8:
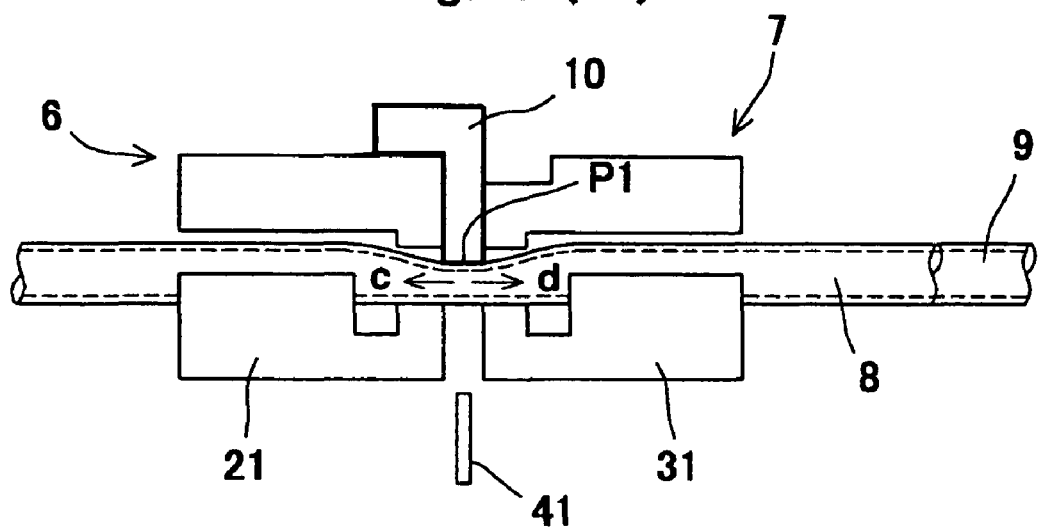
FIG. 8 is an explanatory drawing showing operation of the main portions of the tube connecting apparatus, FIG. 8(A) showing operation 2 and FIG. 8(B) showing operation 3.
Figure 8:
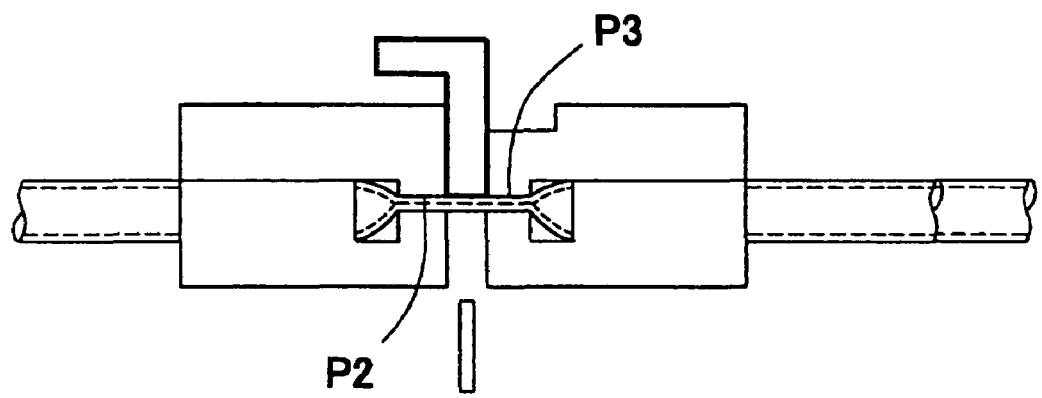

An operator opens the covering body 24 of the first clamp 6 and the covering body 34 of the second clamp 7 to put (set) the tubes 8, 9 into the grooves 22, 23. When the operator opens either one of the covering body 24 of the first clamp 6 or the covering body 34 of the second clamp 7, because the shaft 19 of the first clamp 6 is inserted into the long hole 40 of the second clamp 7, another of the covering body 24 of the first clamp 6 or the covering body 34 of the second clamp 7 is linked to open approximately at the same time. Then, the operator carries out operation for closing the covering body 24 of the first clamp 6 and the covering body 34 of the second clamp 7 to the put tubes 8, 9. (See FIG. 7.) When the operator closes either one of the covering body 24 of the first clamp 6 or the covering body 34 of the second clamp 7, because the shaft 19 of the first clamp 6 is inserted into the long hole 40 of the second clamp 7, another of the covering body 24 of the first clamp 6 or the covering body 34 of the second clamp 7 is linked to close approximately at the same time. When the operator further continues to carry out the operation for closing the covering body 24 and the covering body 34, the tip portion 12 of the tube-pushing member 10 firstly abuts and then deforms the tubes 8, 9, which are put in a parallel state at a first position P1 that is an abutting position, to a flat state. (See FIG. 8(A).) At this moment, blood inside the tubes 8, 9 at a portion which was pressed by the tube-pushing member 10 is pushed out such that it is excluded in directions of an arrow c and an arrow d in FIG. 8(A).

Subsequently, when the operation for closing the covering body 24 and the covering body 34 is carried out further, the pawl member 29 engages the roller 20 of the locking mechanism in the first clamp 6, thereby the covering body 24 is locked so as not to open. In this state, the first clamp 6 presses and holds the tubes 8, 9 to a flat state with predetermined pressing force at a second position P2 which is adjacent to the first position P1. At this time, the tube-pushing member 10 disposed so as to contact the first clamp 6 also presses the tubes 8, 9 to an almost squashed state (a state that blood inside the tubes hardly exits) according to the energizing force of unillustrated springs in the same manner as the first clamp 6. (See FIG. 8(B).)

Figure 10A:
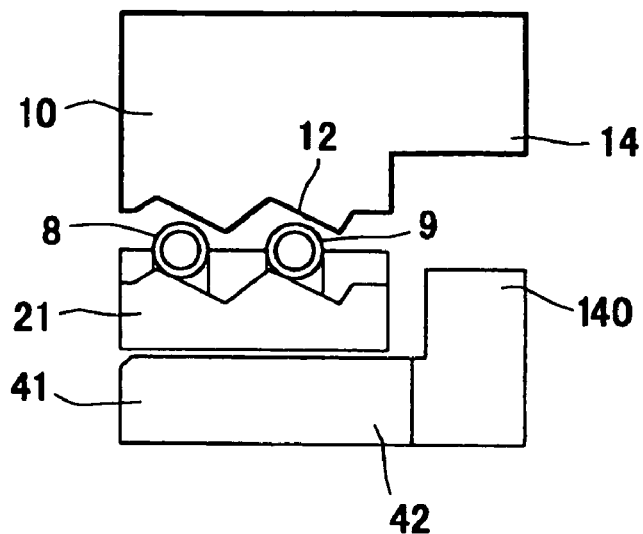
FIG. 10 is a side view showing evacuation movement of a tube-pushing member, FIG. 10(A) showing a state just before a tip portion of the tube-pushing member presses tubes to a flat state, FIG. 10(B) showing a state that the tip portion of the tube-pushing member presses the tubes to a flat state, and FIG. 10(C) showing a state that a wafer cuts the tubes held in a flat state.
Figure 10B:
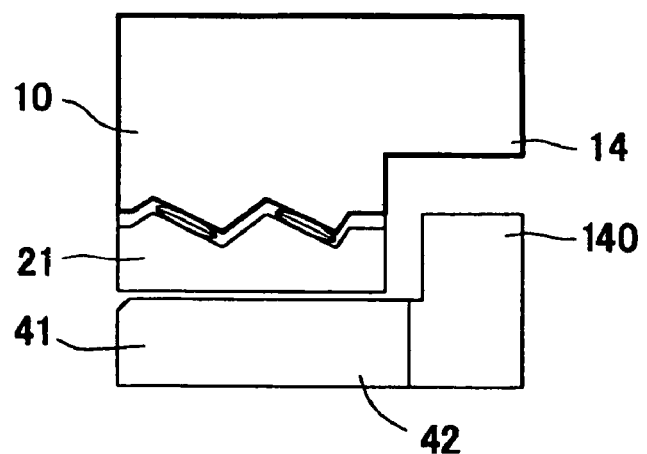

FIG. 10(A) shows a state that the covering body 24 of the first clamp 6 is closed to the tubes 8, 9 put in the grooves 22, 23 and a state just before the tip portion 12 of the tube-pushing member 10 presses tubes 8, 9 to a flat state. As shown in FIG. 10(B), when the operator continues the operation for closing the covering body 24, the tip portion 12 of the tube-pushing member 10 presses the tubes 8, 9 to a flat state. At this time, pressing operation by the first clamp 6 and the second clamp 7 to the tubes 8, 9 is carried out continuously in a linked manner.

Figure 13C:
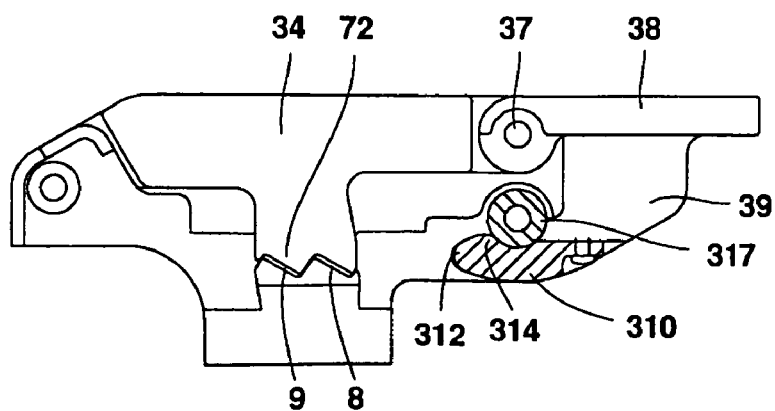
Figure 14C:
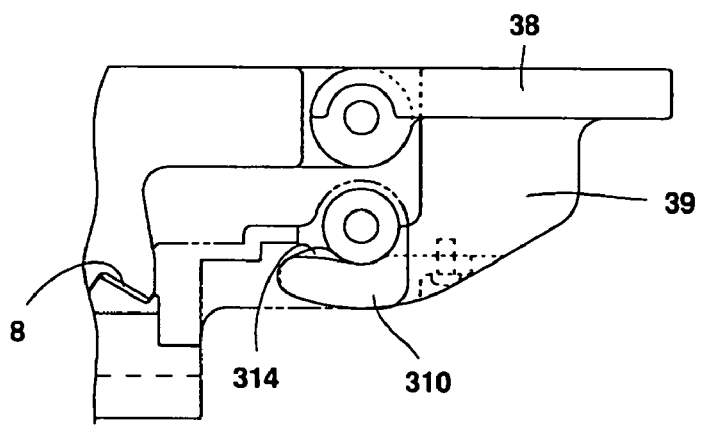
Figure 15A:
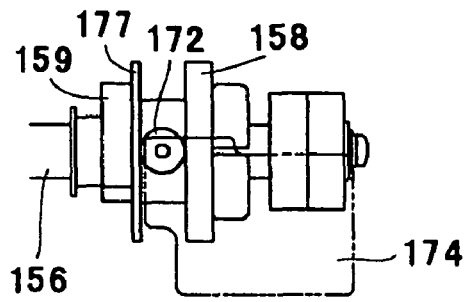
FIG. 15 is an enlarged plan view around a cam which regulates movement of the second clamp, FIG. 15(A) showing an initial state, FIG. 15(B) showing a state that connection operation is completed, FIG. 15(C) showing a state that a notched portion is opposed to a bearing
FIG. 15(D) is a state that the second clamp is moved to an evacuated position.
Figure 15B:
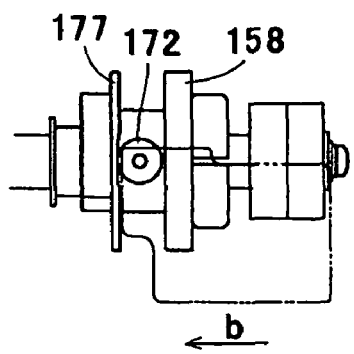
Figure 15C:
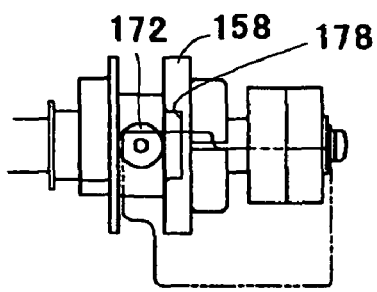
Figure 15D:
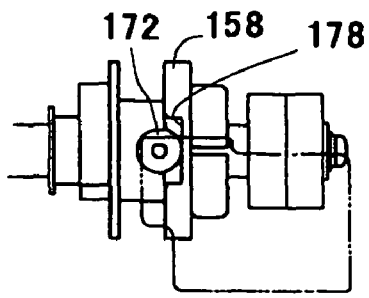
Figure 16:
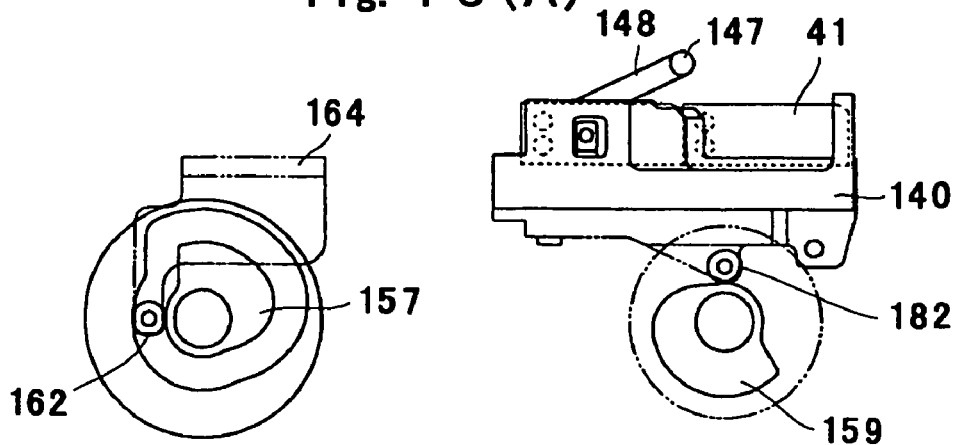
FIG. 16 is a side view of a cam which regulates movement of the first clamp and a cam which regulates movement of the wafer holder, FIG. 16(A) showing an initial state, FIG. 16(B) showing a state of cutting operation and FIG. 16(C) showing a state that cutting is finished and connecting is started.
Figure 16:
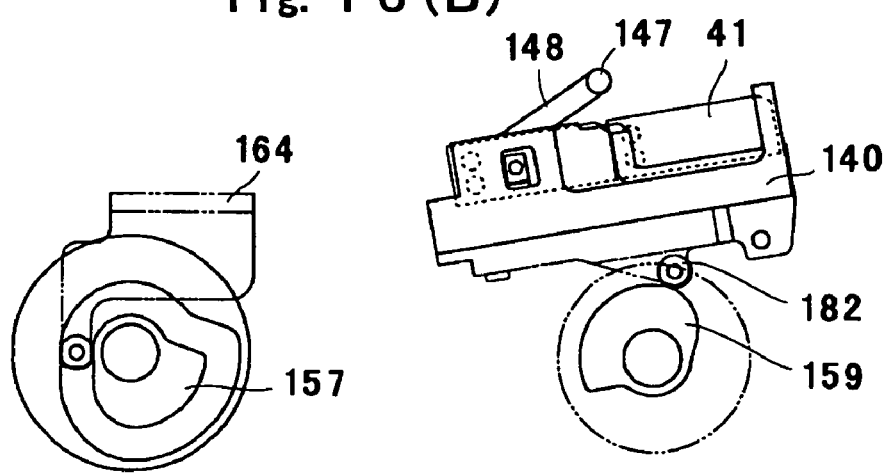
Figure 16:
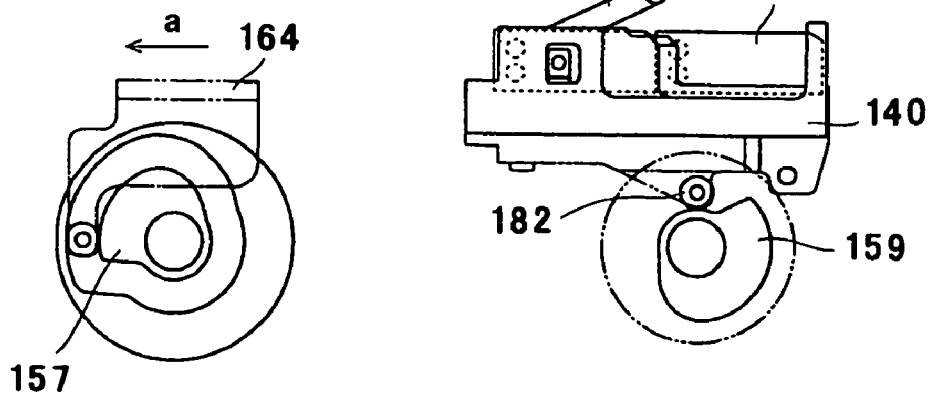

Further, because movement of the second clamp 7 is linked with movement of the first clamp 6 due to insertion of the shaft 19 into the long hole 40, operation for closing the covering body 34 of the second clamp 7 is carried out approximately at the same time of the operation for closing the covering body 24 of the first clamp 6. When the pawl member 39 of the locking mechanism in the second clamp 7 engages the roller 30 and the covering body 34 is locked so as not to open, the second clamp 7 which is located so as to contact the tube-pushing member 10, in the same manner as the first clamp 6, presses and holds the tubes 8, 9 to a flat state in an almost squashed state (a state that blood inside the tubes hardly exits) with predetermined pressing force at a third position P3 which is adjacent to the first position P1 and which is a position opposing to the second position P2 via the first position P1. Thus, blood inside the tubes 8, 9 from the second position P2 to the third position P3 via the first position P1, namely, blood inside the tubes 8, 9 at portions being equivalent from a portion pressed by the first clamp 6 to a portion pressed by the second clamp 7 via the tube-pushing member 10 is almost excluded (See FIG. 8(B).), pressing and holding operation of the tubes 8, 9 is finished. FIGS. 13(C) and 14(C) show the first clamp 6, the tube-pushing member 10 and the wafer holder 140 in the finished state, and FIGS. 15(A) and 16(A) show a moving state of the cam 158 and the cams 157, 159.

When an operator pushes the start button 193 of the apparatus 1, the CPU 191 fetches a start signal via the start button controlling section and executes feeding operation for wafer 41 from the wafer cassette 120 according to the wafer feeding mechanism 100.

As stated above, the wafer feeding member 115 which is moved by rotation driving of the pulse motor 110 moves reciprocally between the wafer feeding start position and the wafer feeding end position according to normal and reverse rotation of the pulse motor 110. At this time, the CPU 191 detects a position of the wafer feeding member 115 located between the wafer feeding start position and the wafer feeding end position at a time of normal rotation of the pulse motor 110 with the transmission type sensor 131 one pulse by one pulse in accordance with the revolving amount of the revolving plate 130 which is linked directly with the rotation of the pulse motor 110. Namely, by detecting the piece to be detected 119 of the wafer feeding member 115 which is located at the wafer feeding start position with the transmission type sensor 132, and based on the wafer feeding start position, by detecting the moving amount of the wafer feeding member 115 through the revolving amount of the revolving plate 130 with the transmission type sensor 131, the CPU 191 grasps as to where the wafer feeding member 115 is located.

The CPU 191 judges as to whether or not the wafer feeding member 115 moves more than a predetermined amount (30 mm in this embodiment, See the wafer feeding member 15 shown by a two dotted line in FIG. 15.) from the wafer feeding start position to a direction of the wafer feeding end position. When a negative judgment is made, the CPU 191 continues to grasp the position of the wafer feeding member 115. Incidentally, in this embodiment, the moving amount of the wafer feeding member 115 for feeding the wafer 41 is set to approximately 55 mm.

When an affirmative judgment is made, the CPU 191 judges as to whether or not a difference between a predetermined number of pulses and an actually detected number of pulses, which is not less than predetermined pulses (ex. 20 pulses), occurred, namely, the CPU 191 judges as to whether or not the actually detected number of pulses was less than 20 pulses to the predetermined number of pulses. When an affirmative judgment is made, the CPU 191 determines that feeding malfunction of the wafer 41 occurred and waits until the reset button is pushed. When a negative judgment is made, the CPU 191 determines that normal feeding was made.

When feeding malfunction of the wafer 41 is determined, the CPU 191 stops driving of the pulse motor 110 and makes the display panel 192 to display an error indication (feeding malfunction of wafer) and display that the wafer is to be removed, and drives the pulse motor 150 by a predetermined amount reversely opposing to the normal driving carried out at the time of a series of tube connecting operation to locate the cam 158 at a predetermined position so that the notched portion 178 formed at the cam 158 faces the bearing 172. (See FIG. 15(C).) Thus, the bearing 172 is ready to advance into the notched portion 178. In other words, the second clamp 7 is allowed to move to an evacuating position in a right direction of an arrow B in FIG. 3 (a direction that allows the second clamp 7 to move in a direction opposite to a direction of the second clamp 7 at the time of connecting the tubes). (In this embodiment, the second clamp 7 is allowed to move by approximately 4 mm.) At this moment, both of the transmission type sensors 195, 196 are in a state that they are shielded by the revolving plate 197. (See FIG. 6(C).)

An operator can move the second clamp 7 to the evacuating position and remove the wafer which caused feeding malfunction such as double feeding of the wafers 41 by accessing a space defined between the first clamp 6 and the second clamp 7. (See FIG. 15(D).) When the operator pushes an unillustrated reset button after finishing the error cancellation operation, the CPU 191 fetches a signal thereof, then drives the pulse motors 110, 150 to reset various mechanisms to an initial state.

When normal feeding of the wafer 41 is determined, the CPU 191 executes cutting/connecting process. In cutting process, as stated above, the CPU 191 judges as to whether or not the wafer 41 reached the predetermined temperature capable of melting the tubes 8, 9 by judging whether or not the predetermined period of time has lapsed from the time that the wafer 41 was inserted into the wafer holder 140 with an internal clock. When a negative judgment is made, the CPU 191 waits until a predetermined time lapses. When an affirmative judgment is made, the CPU 191 drives the pulse motor 150. This makes the cam 158 and the cams 157, 159 to start rotating in a predetermined direction, yet the cam 158 retains a state shown in FIG. 15(A) for a predetermined period of time. During this period, the wafer holder 140 swings according to rotation of the cam 159 to ascend a predetermined distance between the first clamp 6 and the second clamp 7. (See FIG. 16(B).) Accompanied by this ascending movement, the roller 147 ascends and the supporting member projection portion 14 which abuts the roller 147 also ascends.

Figure 9A:
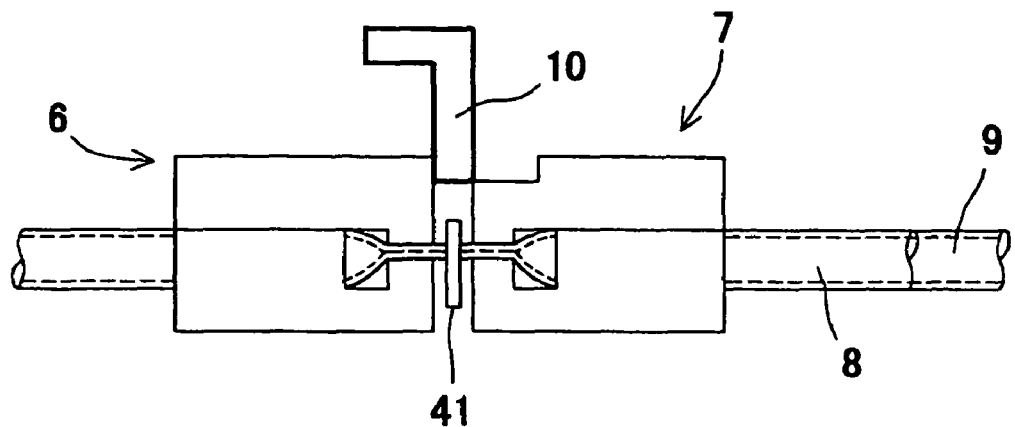
FIG. 9 is an explanatory drawing showing operation of the main portions of the tube connecting apparatus, FIG. 9(A) showing operation 4, FIG. 9(B) showing operation 5 and FIG. 9(C) showing operation 6.
Figure 10C:
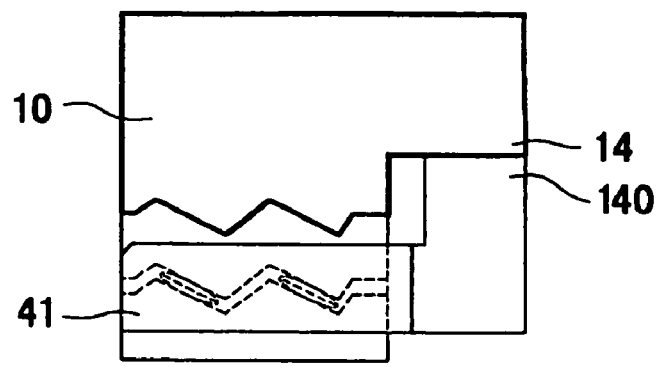

As shown in FIG. 9(A), the projection portion 148 which has the metal roller 147 at its tip and which forms a part of the wafer holder 140 pushes up a part of the tube-pushing member 10 which pressed the tubes 8, 9 at the first position P1, and the heated wafer 41 which is held by the wafer holder 140 advances to the gap between the first position P1 and the second position P2 (between the first clamp 6 and the second clamp 7) to cut the two tubes 8, 9. At this time, the tube-pushing member 10 is brought in a state that it is located at the evacuating position to the wafer 41. (See FIG. 10(C).) FIG. 13 shows a state that the wafer holder 140 ascends (swings) and the wafer 41 cuts the tubes 8, 9 set at the predetermined positions. On the other hand, the cam 157 rotates (See FIG. 16(B).) from a state shown in FIG. 16(A), but the first clamp 6 (the supporting table 164) is kept in a stopped state in the same manner as the second clamp 7 (the supporting table 174) shown in FIG. 15(A).

The CPU 191 further continues to drive the pulse motor 150. The wafer holder 140 retains a state shown in FIG. 16(B), while the first clamp 6 (the supporting table 164) moves by a predetermined distance (8 mm) in a direction of an arrow a of a left side of the FIG. 16(C) (a direction toward the arrow A in FIG. 3, a direction of the arrow X in FIG. 17) according to rotation of the cam 157. At this moment, the positions of the cut tubes are relatively changed and the portions to be connected face each other. At this time, as shown in FIG. 17, the wafer 41 which has cut the tubes 8, 9 is held at a cutting position thereof in the stopped state. Further at this time, the shaft 19 of the first clamp 6 moves inside the long hole 40 of the second clamp 7 in a state that the shaft 19 is inserted in the long hole 40.

Figure 9B:
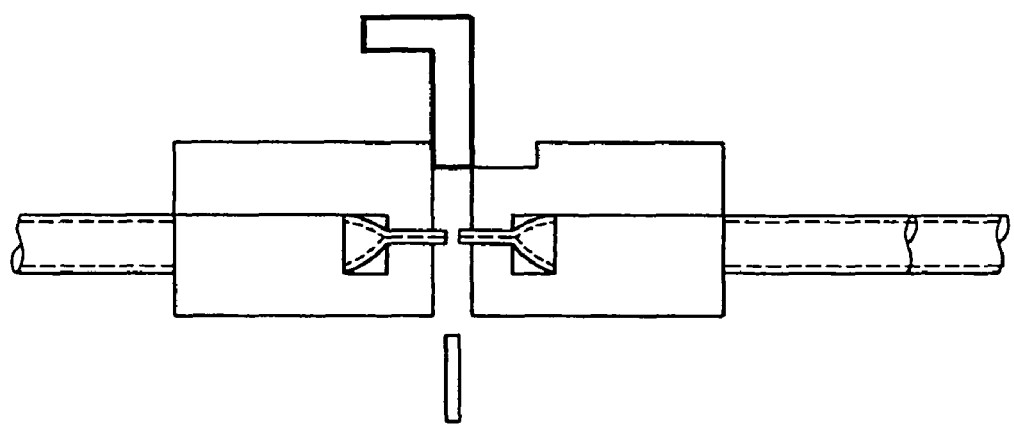
Figure 9C:
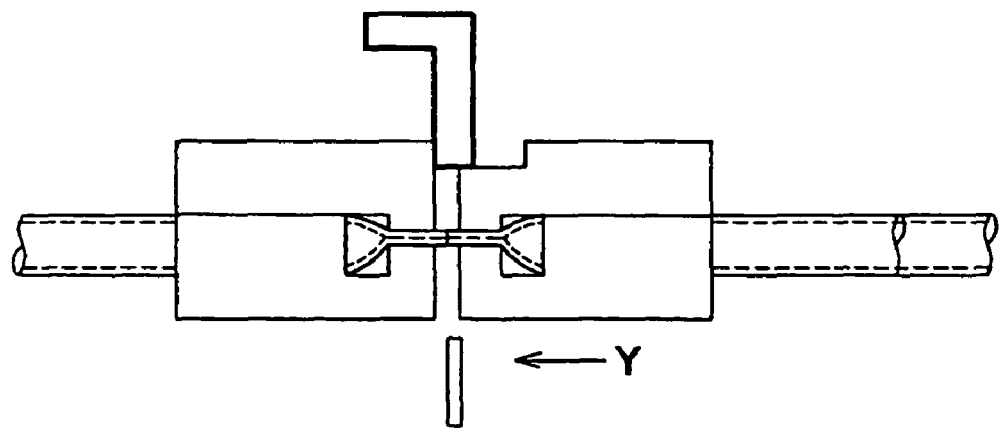

Subsequently, the wafer holder 140 swings to descend (See FIG. 16(C).) according to rotation of the cam 159, but the tube-pushing member 10 is held at the above stated evacuating position in a stopped state. (See FIG. 9(B).) On the other hand, because the bearing 172 adjacent to the cam 158 slides along a shape of the flange portion 177, the second clamp 7 (the supporting table 174) moves by a predetermined distance (0.6 mm) in a direction of an arrow b in FIG. 15(B) (a left direction of an arrow B in FIG. 3, a direction of an arrow Y in FIG. 9(C)). Thus, the connecting operation of the tubes 8, 9 is finished. At this time, as shown in FIG. 6(B), the notch 198 is located at a position that faces the transmission type sensor 196, and the CPU 191 confirms a predetermined state (a state that the first clamp 6 is dislocated from the second clamp 7) to stop driving of the pulse motor 150.

When an operator lifts the plate piece 38 provided at the tip side of the covering body 34 to remove the tube(s) that the connecting operation is finished from a main body of the apparatus, the hook portion B 312 having the flexure property bends to release engagement with the roller B 317 in order to cancel locking according to the locking mechanism. Accordingly, the covering body 34 becomes an opened state. (See FIG. 12.) At this time, the covering body 34 and the covering body 24 are in a state that their relative positions are changed or dislocated, however, because the shaft 19 is inserted in the long hole 40, when the operator lifts the covering body 34, the covering body 24 is lifted approximately at the same time linked with lifting of the covering body 34. (Even he/she lifts the covering body 24, the covering body 34 is lifted linked with the covering body 24.) Incidentally, linked with the opening operation for the covering body 34, pushing to the tube 8, 9 due to the tube-pushing member 10 is also canceled.

(Effects and the Like)

Next, effects and the like of the tube connecting apparatus 1 in this embodiment will be explained.

In the tube connecting apparatus 1 of this embodiment, the tube-pushing member 10 whose tip portion 12 is protruded a little more than the pressure closing member 62 of the first clamp 6 is disposed between the first clamp 6 and the second clamp 7, and the tube-pushing member 10 presses the tubes 8, 9 so as to push out the residual blood in the tubes at the pushing portion prior to pressing of the first clamp 6 and the second clamp 7 in order to exclude the blood. Accordingly, the tube connecting apparatus 1 can connect the tubes each other without being influenced by the blood in the tubes at the time of cutting and then connecting the tubes each other.

Further, in the tube connecting apparatus 1 of this embodiment, the tip ends of the pawl members 29, 39 which constitute the hook sections 300 and 310 set up at the first upper jaw portion 50 and the second upper jaw portion 60 that press and hold the tubes 8, 9, are divided into a plurality of portions, and among the portions, the protruded portions 304 and 314 for preventing back-tracking are formed at the hook portions B 302 and 312. At the same time, the resin members (POM) capable of elastic deformation are used for the hook portions B 302, 312, and such a structure that the hook portions exhibit a function of a plate spring is employed (The hook portions are long in a direction orthogonal to the tubes 8, 9 and the end portions thereof are fixed by screws.) in order to promote their flexure property. Accordingly, durability for members that constitute the locking mechanisms is improved, while maintaining pressing force against the tubes 8, 9. Further, operability and work efficiency of the tube connecting apparatus 1 can be improved since pressing force (load force) according to an operator is lowered at a time of locking and unlocking comparing with the conventional tube connecting apparatus as shown in the equation (1). Furthermore, in the tube connecting apparatus 1 of the present embodiment, since the roller B 307, 317 rides over the protruded portions 304, 314 by satisfying the relationship shown in the equation (1) to allow the protruded portions 304, 314 to advance toward their locking positions, and since reaction force when the hook portions B 302, 312 bend according to external force is set larger than or equal to the load force of the rollers B 307, 317 against the protruded portions 304, 314, the protruded portions 304, 314 are retained at the locking positions while maintaining appropriate pressing force against the tubes 8, 9, so that locking operation by the locking mechanisms is maintained successively.

Moreover, in the tube connecting apparatus 1 of this embodiment, the resin member (POM) is also used for the rollers B 307, 317 of the first lower jaw portion 70 and the second lower jaw portion 80 which engages the hook portions B 302, 312 and which has the latch function. Accordingly, since the apparatus can avoid lowering of locking force at the locking mechanisms even in long-term use unlike the conventional tube connecting apparatus that causes parts to wear away at a time of engagement and contact operation between metal-made members each other in locking, a tube connecting apparatus having high durability can be provided.

Furthermore, in the tube connecting apparatus 1, at the time of connecting the tubes, the positions of the end portions of the cut tubes are changed (shifted) relatively in the state of contacting the wafer 41 such that the end portions to be connected of the tubes face each other, and the end portions to be connected of the tubes are contacted with each other for connecting the tubes at the same time of the descending movement of the wafer 41. However, in this embodiment, since the structure of the above stated locking mechanisms is employed, smooth cutting operation as well as stable and reliable connecting operation to the tubes 8, 9 can be secured.

Moreover, in the tube connecting apparatus 1 of this embodiment, since the structure for releasing the tube-pushing member 10, linked with the opening operation of the covering bodies 24, 34, is employed, the tube-pushing member 10 can be reset to the initial state at a time of starting the next connecting of the tubes carried out by an operator. Accordingly, a series of processing time is shortened and work efficiency can be improved.

Further, in the tube connecting apparatus 1 of this embodiment, the piece to be detected 119 of the wafer feeding member 115 which is located at the wafer feeding start position is detected by the transmission type sensor 132, and from the wafer feeding start position, the moving amount of the wafer feeding member 115 is detected by the revolving plate 130 and the transmission type sensor 131. Accordingly, a feeding amount (feed) of the wafer 41 can be detected precisely. Furthermore, since the feeding malfunction is judged when the actually detected number of pulses is more than the predetermined number of pulses, detection accuracy of the feeding malfunction of the wafer 41 can be improved.

Furthermore, in the tube connecting apparatus 1, since the structure that the bearing 172 is capable of advancing into the notched portion 178 when the feeding malfunction of the wafer 41 caused is employed, an operator can cancel the feeding malfunction of the wafer 41 by moving the second clamp 7 to the evacuating position. Conventionally, when this type of error was occurred, the apparatus was returned to a factory as malfunction of the apparatus to remove the wafer which caused the feeding malfunction through disassembling the apparatus. However, according to the tube connecting apparatus 1, since an operator can easily carry out error cancellation due to the feeding malfunction of the wafer, operability and reliance to the apparatus can be improved.

Further, in the tube connecting apparatus 1, since the wafer feeding mechanism 100 is stopped when the full state of the waste box 142 is detected by the transmission type sensor 143, even if automatic thrusting (feeding) structure for the wafer(s) is employed, the wafer jammed by the following wafer at the conveying path can be prevented. Furthermore, in the tube connecting apparatus 1, whether or not the first clamp 6 and the second clamp 7 can hold the tubes 8, 9 in parallel with each other is judged according to the transmission type sensor 195, and when the clamps are not parallel (not in the initial positions), the apparatus is not started as it is but the apparatus is started after the first clamp 6 and second clamp 7 are returned to the appropriate initial positions according to pushing of the reset button. Accordingly, regular cutting and connecting operation can be always secured.

Moreover, in the tube connecting apparatus 1, since the shaft 19 of the first clamp 6 can be inserted into the long hole 40 of the second clamp 7, not only in a state that the first clamp 6 and the second clamp 7 are located at the initial positions (a time of setting the tubes) but also in a state that relative positions thereof are changed (a time of finishing connecting the tubes), when either one of the covering body 24 of the first clamp 6 or the covering body 34 of the second clamp 7 is opened/closed, another of the covering body 24 of the first clamp 6 or the covering body 34 of the second clamp 7 is opened/closed approximately at the same time in a linking manner. Accordingly, operability or handling efficiency is improved. Further, in the tube connecting apparatus 1, the cam structure is employed instead of the conventional movement mechanism(s) which moves directly the first clamp 6 and the second clamp 7 in the X, Y directions such as an X, Y table or the like. Accordingly, downsizing of the apparatus per se can be realized.

Further, the tube connecting apparatus 1 can realize wet-to-wet connecting between the tubes easily, uniformly and rapidly under a sterilized condition only by putting the tubes 8, 9 in which blood is contained and sealed into the grooves 22, 23, 32 and 33 and locking the covering bodies 24, 34 with the locking mechanisms. Because such a tube connecting apparatus has been requested to realize from a public view, an industrial value thereof seems to be extremely high.

Incidentally, in this embodiment, the stainless steel for the base portions of the pawl members 29, 39, the hook portions A 301, 311 and the hook portions C 303, 313 and the POM for hook portions B 302, 312 and the rollers B 307, 317 were exemplified. However, the present invention is not limited to the same. A metal-made member having high rigidity such as aluminum alloy and the like may be used for the hook portion A 301 and the like, and other resin members having small rigidity may be used for the hook portion B 302 and the like.

Further, in this embodiment, an example that the projection portion 148 is formed integrally with the wafer holder 140 was shown, however, the projection portion 148 and the wafer holder 140, each being a separate member, may be fixed so as to be unified. In a case that the projection portion 148 is formed to be slanted like this embodiment, unification (integration) of the separated two members can make a cost for parts lower.

Further, in this embodiment, the protruded portions 304, 314 were exemplified as a protruded portion. However, it is sufficient for the protruded portion of the present invention to protrude so that the protruded portion can maintain an engagement relationship with the rollers 307, 317 as engagement members, respectively, and it is sufficient for a shape thereof to protrude from the surroundings, even if the shape may have a protruded shape or a projected shape which protrudes milder than the protruded shape.

Furthermore, in this embodiment, an example that connecting of the tubes in which blood is contained and sealed each other was shown, however, the present invention is not restricted to this. The present invention may be applied either in a case of connecting between a tube in which blood is contained and an empty tube or in a case of connecting between empty tubes in which blood is not contained; both have been carried out conventionally. Further, an example that feeding operation of the wafer 41 from the wafer cassette 120 by the wafer feeding mechanism 100 is started by pushing the start button 193 was exemplified, however, the present invention is not limited to this. The feeding operation may be initiated by pushing the reset button. Furthermore, a structure that a groove is formed at a second pressing unit, more concretely, the long hole 40 is formed at the second clamp 7 was shown, however, the present invention is not limited to this. A structure that a dented portion is formed at a bottom of the plate piece 38 of the second clamp may be employed.

Further, in this embodiment, the tube connecting apparatus which connects the two tubes in which blood is contained and sealed was shown. However, the present invention is not restricted to the same. It is also applicable to a tube connecting apparatus which connects three tubes or more, or a tube connecting apparatus which connects tubes in which liquid other than blood is contained and sealed properly each other.

Moreover, in this embodiment, a structure that the wafer holder 140 can hold two wafers was exemplified, however, the present invention is not limited to the same. The wafer holder may hold a single wafer, or, three wafers or more.

And, in this embodiment, the saw-shaped pressure closing members 61, 62, 71, 72 and the saw-shaped tube-pushing member 10 were explained. However, since it is sufficient for these members to have a function for pushing out and excluding blood in the tubes 8, 9, they may press and close the tubes 8, 9, for example, at their horizontal faces. Further, the wafer 41 is not limited to the self-heating typed one. For example, the wafer may have a structure heated by a heat source such as an electric heater.

DESCRIPTION OF NUMERALS

1 tube connecting apparatus
6 first clamp (holding unit, first holding section)
7 second clamp (holding unit, second holding section)
8, 9 tube
20, 30 roller
28, 38 plate piece (a part of a hook section)
29, 39 pawl member (a part of a hook section)
41 wafer (a part of a cutting unit)
50 first upper jaw portion (movable clamp section)
60 second upper jaw portion (movable clamp section)
70 first lower jaw portion (placement clamp section)
80 second lower jaw portion (placement clamp section)
140 wafer holder (a part of a cutting unit)
150 pulse motor (a part of a movement unit)
156 driving shaft (a part of a movement unit)
200 drive-conveying mechanism (a part of a movement unit, a part cutting unit)
300, 310 hook section
301, 311 hook portion A (a part of a hook section)
302, 312 hook portion B (a part of a hook section, elastic member)
303, 313 hook portion C (a part of a hook section)
304, 314 protruded portion
306, 316 roller A
307, 317 roller B (engagement member)
308, 318 roller C

What is claimed is:

1. A tube connecting apparatus which connects flexible tubes to each other, comprising:
    a holding unit having a placement clamp section at which the tube is placed, a movable clamp section which is movable in a direction of pressing the tube which is placed at the placement clamp section and in a direction of separating from the tube, and a hook section which is set up at the movable clamp section and which engages the placement clamp section to maintain a pressing state of the movable clamp section against the tube;
    a cutting unit which cuts the tubes held in a flat state by the holding unit; and
    a movement unit which moves the holding unit to change relatively positions of the tubes cut by the cutting unit such that end portions to be connected face each other,
    wherein the holding unit has a plurality of divided hook portions at the hook section in a direction orthogonal to a longitudinal direction of the tube placed at the placement clamp section, and wherein at least one of the hook portions is made of an elastic member which maintains engagement with the placement clamp section, the elastic member having a protruded portion at one side which protrudes relative to other hook portions and having an other side fixed to the hook section,
    wherein the holding unit has a first holding section and a second holding section which are disposed along a longitudinal direction of the tubes placed at the placement clamp section,
    wherein the first holding section has a shaft which protrudes from an end face disposed at a side of the second holding section of the movable clamp section, and the second holding section has a long hole formed at a side of the first holding section of the movable clamp section and into which the shaft is inserted, and
    wherein the movement unit moves one of the first holding section and the second holding section relative to an other of the first holding section and the second holding section, the shaft remaining inserted within the long hole during and after the movement of the one of the first holding section and the second holding section relative to the other of the first holding section and the second holding section.

2. A tube connecting apparatus according to claim 1, wherein the cutting unit cuts the tubes between the first holding section and the second holding section.

3. A tube connecting apparatus according to claim 2, wherein the movement unit moves at least one of the first holding section and the second holding section in a direction of the longitudinal direction of the tubes placed at the placement clamp section and in a direction orthogonal to the tubes.

4. A tube connecting apparatus according to claim 3, wherein the elastic member is made of resin having a flexure property of bending so as to change its self-shape according to external pressure.

5. A tube connecting apparatus according to claim 4, wherein the elastic member is disposed at a center of the hook portions which are provided parallel, and wherein a material of the other hook portions is made of metal.

6. A tube connecting apparatus according to claim 1, wherein the elastic member is disposed at a center of the hook portions which are provided parallel, and wherein a material of the other hook portions is made of metal.

7. A tube connecting apparatus according to claim 1, wherein the placement clamp section has an engagement member which engages the protruded portion of the elastic member, and wherein a material of the engagement member is made of resin.

8. A tube connecting apparatus according to claim 7, wherein the engagement member is a rotatable roller, and wherein the protruded portion of the elastic member slides to contact a circumferential surface of the roller to be located to an engagement maintaining position at which the protruded portion maintains engagement with the roller.

* * * * *